US010537646B2

(12) United States Patent
Fima et al.

(10) Patent No.: US 10,537,646 B2
(45) Date of Patent: *Jan. 21, 2020

(54) PEGYLATED OXM VARIANTS

(71) Applicant: OPKO Biologics Ltd., Nes Ziona (IL)

(72) Inventors: Udi Eyal Fima, Beer-Sheva (IL); Oren Hershkovitz, Rishon Lezion (IL)

(73) Assignee: OPKO Biologics Ltd., Kiryat Gat (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/405,597

(22) PCT Filed: Jun. 4, 2013

(86) PCT No.: PCT/IL2013/050481
§ 371 (c)(1),
(2) Date: Dec. 4, 2014

(87) PCT Pub. No.: WO2013/183052
PCT Pub. Date: Dec. 12, 2013

(65) Prior Publication Data
US 2015/0148289 A1 May 28, 2015

Related U.S. Application Data

(60) Provisional application No. 61/655,367, filed on Jun. 4, 2012.

(51) Int. Cl.
*A61K 38/26* (2006.01)
*C07K 14/605* (2006.01)
*C07K 1/00* (2006.01)
*A61K 47/60* (2017.01)
*A61K 38/22* (2006.01)

(52) U.S. Cl.
CPC ............. *A61K 47/60* (2017.08); *A61K 38/22* (2013.01); *A61K 38/26* (2013.01); *C07K 1/00* (2013.01); *C07K 14/605* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Leute |
| 3,984,533 A | 10/1976 | Uzgiris |
| 3,996,345 A | 12/1976 | Schwarzberg |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Kary |
| 4,801,531 A | 1/1989 | Frossard |
| 4,879,219 A | 11/1989 | Schoemaker et al. |
| 4,880,634 A | 11/1989 | Speiser |
| 5,011,771 A | 4/1991 | Bellet et al. |
| 5,192,659 A | 3/1993 | Simons |
| 5,272,057 A | 12/1993 | Bhatia et al. |
| 5,281,521 A | 1/1994 | Lee et al. |
| 5,464,764 A | 11/1995 | Capecchi et al. |
| 5,487,992 A | 1/1996 | Capecchi et al. |
| 5,643,575 A | 7/1997 | Greenwald et al. |
| 5,681,567 A | 10/1997 | Greenwald et al. |
| 5,858,975 A | 1/1999 | Yano et al. |
| 5,919,455 A | 7/1999 | Greenwald et al. |
| 5,929,177 A | 7/1999 | Kataoka et al. |
| 5,932,447 A | 8/1999 | Siegall |
| 6,113,906 A | 9/2000 | Greenwald et al. |
| 6,433,135 B1 | 8/2002 | El-Tayar et al. |
| 6,504,005 B1 | 1/2003 | Fridkin et al. |
| 7,585,837 B2 | 9/2009 | Shechter et al. |
| 8,343,910 B2 | 1/2013 | Shechter et al. |
| 9,119,883 B2 | 9/2015 | Shechter et al. |
| 2002/0141985 A1 | 10/2002 | Pittner et al. |
| 2006/0011920 A1 | 1/2006 | Kim |

(Continued)

FOREIGN PATENT DOCUMENTS

EP 0374257 A1 6/1990
EP 0167825 8/1990

(Continued)

OTHER PUBLICATIONS

Druce et al. Investigation of structure-activity relationships of oxyntomodulin (Oxm) using Oxm analogs. Endocrinology, 150(4):1712-1721, Apr. 2009. (Year: 2009).*
Adrian, T.- E., et al. "Human distribution and release of a putative new gut hormone, peptide YY." Gastroenterology 89.5: 1070-1077 (1985).
Albericio et al., "An improved synthesis of N-[(9-hydroxymethyl)-2-fluorenyl] succinamic acid (HMFS), a versatile handle for the solid-phase synthesis of biomolecules." Synthetic Communications 31.2: 225-232 (2001).
Anonymous "Long Acting Reversible PEGylated Oxyntomodulin—MOD-6030", Apr. 19, 2012, pp. 1-14; Retrieved from the Internet: URL:http://www.sec.gov/Archives/edgar/data/1268659/000114420412022748/v309878_ex99-1.htm [retrieved on Jan. 9, 2015].

(Continued)

*Primary Examiner* — Elizabeth C. Kemmerer
*Assistant Examiner* — Regina M DeBerry
(74) *Attorney, Agent, or Firm* — Mark S. Cohen; Pearl Cohen Zedek Latzer Baratz LLP

(57) ABSTRACT

A composition which includes oxyntomodulin and polyethylene glycol polymer (PEG polymer) linked via a reversible linker such as 9-fluorenylmethoxycarbonyl (Fmoc) or 2-sulfo-9-fluorenylmethoxycarbonyl (FMS) is disclosed. Pharmaceutical compositions comprising the reverse pegylated oxyntomodulin and methods of using same are also disclosed.

7 Claims, 12 Drawing Sheets

Specification includes a Sequence Listing.

(56) References Cited

U.S. PATENT DOCUMENTS

| | | | |
|---|---|---|---|
| 2006/0171920 A1* | 8/2006 | Shechter | A61K 47/48215 424/85.4 |
| 2006/0189522 A1 | 8/2006 | Bloom et al. | |
| 2009/0298757 A1 | 12/2009 | Bloom et al. | |
| 2010/0041867 A1 | 2/2010 | Shechter et al. | |
| 2010/0144617 A1 | 6/2010 | Sinha Roy et al. | |
| 2011/0034374 A1 | 2/2011 | Bloom et al. | |
| 2011/0152182 A1 | 6/2011 | Alsina-Fernandez et al. | |
| 2011/0166063 A1* | 7/2011 | Bossard | A61K 38/10 514/5.9 |
| 2013/0116175 A1 | 5/2013 | Shechter et al. | |
| 2014/0349922 A1 | 11/2014 | Fima et al. | |
| 2015/0057219 A1 | 2/2015 | Shechter et al. | |
| 2015/0119320 A1 | 4/2015 | Fima et al. | |
| 2015/0148289 A1 | 5/2015 | Fima et al. | |
| 2015/0258208 A1 | 9/2015 | Fima et al. | |

FOREIGN PATENT DOCUMENTS

| | | |
|---|---|---|
| JP | 3148298 | 3/2001 |
| WO | WO 1989/010756 | 11/1989 |
| WO | WO 1998/005361 | 2/1998 |
| WO | WO 2002/007859 | 1/2002 |
| WO | WO 2002/036067 | 5/2002 |
| WO | WO 2004/089280 | 10/2004 |
| WO | WO-2006134340 * | 12/2006 |
| WO | WO 2007/100535 A | 9/2007 |
| WO | WO 2009/069983 A2 | 6/2009 |
| WO | WO 2010/033207 | 3/2010 |
| WO | WO 2010/107256 A2 | 9/2010 |
| WO | WO 2011/087671 A1 | 7/2011 |
| WO | WO 2011/087672 | 7/2011 |
| WO | WO 2012/101619 | 8/2012 |
| WO | WO 2012/167251 | 12/2012 |
| WO | WO 2012/173422 | 12/2012 |
| WO | WO 2013/157002 | 10/2013 |
| WO | WO 2013/183052 | 12/2013 |

OTHER PUBLICATIONS

Baggio et al., "Oxyntomodulin and Glucagon-Like Peptide-1 Differentially Regulate Murine Food Intake and Energy Expenditure." Gastroenterology 127: 546-558 (2004).
Bailon et al. "Rational design of a potent, long-lasting form of interferon: a 40 kDa branched polyethylene glycol-conjugated interferon α-2a for the treatment of hepatitis C." Bioconjugate Chemistry 12.2: 195-202 (2001).
Bailon et al., "Polyethylene glycol-conjugated pharmaceutical proteins." Pharmaceutical Science & Technology Today 1.8: 352-356 (1998).
Baker, "Pegylated interferon plus ribavirin for the treatment of chronic hepatitis C." Reviews in Gastroenterological Disorders 3.2: 93-109 (2003).
Batterham et al., "Inhibition of food intake in obese subjects by peptide YY3-36." New England Journal of Medicine 349.10: 941-948 (2003).
Batterham et al., "Gut hormone PYY3-36 physiologically inhibits food intake." Nature 418.6898: 650-654 (2002).
Bianchi et al. "A PEGylated analog of the gut hormone oxyntomodulin with long-lasting antihyperglycemic, insulinotropic and anorexigenic activity", Bioorg Med Chem. Nov. 15, 2013;21(22):7064-73.
Bitter et al. "Expression and secretion vectors for yeast." Methods in enzymology 153: 516-544 (1987).
Booth et al., "The use of a 'universarl'yeast expression vector to produce an antigenic protein of Mycobacterium leprae." Immunology Letters 19.1: 65-69 (1988).
Brisson et al., "Expression of a bacterial gene in plants by using a viral vector." Nature 310.5977: 511-514 (1984).
Broberger et al., "Subtypes Y1 and Y2 of the neuropeptide Y receptor are respectively expressed in pro-opiomelanocortin-and neuropeptide-Y-containing neurons of the rat hypothalamic arcuate nucleus." Neuroendocrinology 66.6: 393-408 (1997).
Broglie et al., "Light-regulated expression of a pea ribulose-1,5-bisphosphate carboxylase small subunit gene in transformed plant cells." Science 224.4651: 838-843 (1984).
Buchwald et al., "Long-term, continuous intravenous heparin administration by an implantable infusion pump in ambulatory patients with recurrent venous thrombosis." Surgery 88.4: 507-516 (1980).
Carter, "Structure of serum albumin." Adv. Protein Chem. 45: 153-203 (1994).
Cohen et al., "Oxyntomodulin suppresses appetite and reduces food intake in humans." Journal of Clinical Endocrinology & Metabolism 88.10: 4696-4701 (2003).
Clark et al., "Long-acting growth hormones produced by conjugation with polyethylene glycol." Journal of Biological Chemistry 271.36: 21969-21977 (1996).
Coruzzi et al., "Tissue-specific and light-regulated expression of a pea nuclear gene encoding the small subunit of ribulose-1, 5-bisphosphate carboxylase." The EMBO Journal 3.8: 1671-1679 (1984).
Cutrone et al., "Identification of critical residues in bovine IFNAR-1 responsible for interferon binding." Journal of Biological Chemistry 276.20: 17140-17148 (2001).
Dakin et al. "Oxyntomodulin inhibits food intake in the rat." Endocrinology 142.10: (2001). 4244-4250.
Dakin et al., "Peripheral oxyntomodulin reduces food intake and body weight gain in rats." Endocrinology 145.6: 2687-2695 (2004).
Dakin et al. "Microsatellite null alleles in parentage analysis", Heredity (2004) 93, 504-509.
Delgado et al., "The uses and properties of PEG-linked proteins." Critical Reviews in Therapeutic Drug Carrier Systems 9.3-4: 249-304 (1991).
Diederichs et al.,"Liposome in kosmetika and arzneimitteln." Pharmazeutische Industrie 56.3: 267-275 (1994).
Druce, et al. "Investigation of structure-activity relationships of Oxyntomodulin (Oxm) using Oxm analogs." Endocrinology 150.4: 1712-1722 (2009).
Eisenberg et al., Physicochemical Chemistry with Aapplications to the Life Sciences. 700-745 (Benjamin Cummings, Menlo Park, CA, 1979).
Eldem et al., "Optimization of Spray-Dried and -Congealed Lipid Micropellets and Characterization of Their Surface Morphology by Scanning Electron Microscopy." Pharmaceutical Research 8.1: 47-54 (1991).
Ellman, "A colorimetric method for determining low concentrations of mercaptans." Archives of Biochemistry and Biophysics 74.2: 443-450 (1958).
Eng et al., "Isolation and characterization of exendin-4, an exendin-3 analogue, from Heloderma suspectum venom. Further evidence for an exendin receptor on dispersed acini from guinea pig pancreas." Journal of Biological Chemistry 267.11: 7402-7405 (1992).
Fehmann et al., "Stable expression of the rat GLP-I receptor in CHO cells: activation and binding characteristics utilizing GLP-I (7-36)-amide, oxyntomodulin, exendin-4, and exendin (9-39)." Peptides 15.3: 453-456 (1994).
Fingl et al., "General Principles." The Pharmacological Basis of Therapeutics (ed. Goodman, LS & Gilman, A,): 1-46 (1975).
Freshney "Culture of Animal Cells—A Manual of Basic Technique", Wiley-Liss, N. Y. (1986), pp. 1-4.
Fuertges et al., "The clinical efficacy of poly (ethylene glycol)-modified proteins." Journal of Controlled Release 11.1: 139-148 (1990).
Fung et al., "Strategies for the preparation and characterization of polyethylene glycol (PEG) conjugated pharmaceutical proteins." Polymer Preprints 38.1: 565-66 (1997).
Gardella et al., "Expression of human parathyroid hormone-(1-84) in Escherichia coli as a factor X-cleavable fusion protein." J. Biol. Chem. 265: 15854-15859 (1990).
Garman et al., "The preparation and properties of novel reversible polymer-protein conjugates 2-ω-Methoxypolyethylene (5000) glycoxymethylene-3-methylmaleyl conjugates of plasminogen activators." FEBS letters 223.2: 361-365 (1987).

(56) References Cited

OTHER PUBLICATIONS

Gershonov et al., "A novel approach for a water-soluble long-acting insulin prodrug: Design, preparation, and analysis of [(2-sulfo)-9-fluorenylmethoxycarbonyl] 3-insulin." Journal of Medicinal Chemistry 43.13: 2530-2537 (2000).
Gershonov et al., "New concept for long-acting insulin: spontaneous conversion of an inactive modified insulin to the active hormone in circulation: 9-fluorenylmethoxycarbonyl derivative of insulin." Diabetes 48.7: 1437-1442 (1999).
Ghatei et al. "Molecular Forms of Human Enteroglucagon in Tissue and Plasma: Plasma Responses to Nutrient Stimuli in Health and in Disorders of the Upper Gastrointestinal Tract." The Journal of Clinical Endocrinology & Metabolism 57.3: 488-495 (1983).
Gilboa et al., "Transfer and expression of cloned genes using retrovial vectors." BioTechniques 4.6: 504-512 (1986).
Glue et al., "Hepatitis C Intervention Therapy Group. Pegylated interferon-alpha2b: pharmacokinetics, pharmacodynamics, safety, and preliminary efficacy data." Clinical Pharmacology & Therapeutics 68.5: 556-567 (2000).
Goke et al., "Exendin-4 is a high potency agonist and truncated exendin-(9-39)-amide an antagonist at the glucagon-like peptide 1-(7-36)-amide receptor of insulin-secreting beta-cells." Journal of Biological Chemistry 268.26: 19650-19655 (1993).
Goodman and Gilman, The Pharmacological Basis of Therapeutics (Goodman, L. S., Gilman, A. G., Limbird, L. E., and Hardman, J. G. Eds.) 9th ed., 1211-1213 (2001).
Goodson, "Dental applications." Medical Applications of Controlled Release 2: 115-138 (1984).
Grandt et al., "Two molecular forms of peptide YY (PYY) are abundant in human blood: characterization of a radioimmunoassay recognizing PYY 1-36 and PYY 3-36." Regulatory Peptides 51.2: 151-159 (1994).
Greenwald et al., "Drug delivery systems employing 1, 4-or 1, 6-elimination: poly (ethylene glycol) prodrugs of amine-containing compounds." Journal of Medicinal Chemistry 42.18: 3657-3667 (1999).
Greenwald, "PEG drugs: an overview." Journal of Controlled Release 74: 159-171 (2001).
Greenwald et al., "Drug delivery systems based on trimethyl lock lactonization: poly (ethylene glycol) prodrugs of amine-containing compounds." Journal of Medicinal Chemistry 43.3: 475-487 (2000).
Greenwald et al., "Effective drug delivery by PEGylated drug conjugates." Avanced Drug Delivery Reviews 55.2: 217-250 (2003).
Greenwood, et al. "The preparation of 131I-labelled human growth hormone of high specific radioactivity." Biochemical journal 89.1: 114 (1963).
Gurley et al., "Upstream sequences required for efficient expression of a soybean heat shock gene." Mol. Cell. Biol. 6.2: 559-565 (1986).
Harris et al., "Effect of pegylation on pharmaceuticals." Nature Reviews Drug Discovery 2.3: 214-221 (2003).
Hartley et al., "The Relation of Free Sulfhydryl Groups to Chromatographic Heterogeneity and Polymerization of Bovine Plasma Albumin." Biochemistry 1.1: 60-68 (1962).
Hazum et al., "Preparation and application of radioiodinated sulfhydryl reagents for the covalent labeling of SH-proteins present in minute quantities." Journal of Biochemical and Biophysical Methods 24.1: 95-106 (1992).
Hershkovitz et al. "MOD-6030, a long-acting dual GLP-1/Glucagon agonist improves glycemic control and induces a prolonged anti-obesity effect in Diet Induced Obesity mice, with a potential once weekly injection in humans", Second Diabetes Summit, Boston MA Apr. 19, 2012.
Holmes et al., "Site specific 1: 1 opioid: albumin conjugate with in vitro activity and long in vivo duration." Bioconjugate Chemistry 11.4: 439-444 (2000).
Holst, Jens Juul. "Enteroglucagon." Annual Review of Physiology 59.1: 257-271 (1997).
International Search Report for PCT Application No. PCTIL2013050481 dated Oct. 11, 2013.

Jarrousse et al. "A Pure Enteroglucagon, Oxyntomodulin (Glucagon 37), Stimulates Insulin Release in Perfused Rat Pancreas", Endocrinology, 1984, 115(1):102-105.
Kalra et al., "Interacting Appetite-Regulating Pathways in the Hypothalamic Regulation of Body Weight 1." Endocrine Reviews 20.1: 68-100 (1999).
Katre, Nandini V. "The conjugation of proteins with polyethylene glycol and other polymers: altering properties of proteins to enhance their therapeutic potential." Advanced Drug Delivery Reviews 10.1: 91-114 (1993).
Kurtzhals et al., "Albumin binding and time action of acylated insulins in various species." Journal of Pharmaceutical Sciences 85.3: 304-308 (1996).
Kurtzhals et al., "Albumin binding of insulins acylated with fatty acids: characterization of the ligand-protein interaction and correlation between binding affinity and timing of the insulin effect in vivo." Biochemical Journal 312: 725-731 (1995).
Kurtzhals et al., "Correlations of receptor binding and metabolic and mitogenic potencies of insulin analogs designed for clinical use." Diabetes 49.6: 999-1005 (2000).
Kurtzhals et al., "Effect of fatty acids and selected drugs on the albumin binding of a long-acting, acylated insulin analogue." Journal of pharmaceutical sciences 86.12: 1365-1368 (1997).
Langer, "New methods of drug delivery." Science 249.4976: 1527-1533 (1990).
Le Quellec et al., "Oxyntomodulin-like immunoreactivity: diurnal profile of a new potential enterogastrone." The Journal of Clinical Endocrinology and Metabolism 74.6: 1405-1409 (1992).
Lee et al., "Drug delivery systems employing 1, 6-elimination: releasable poly (ethylene glycol) conjugates of proteins." Bioconjugate Chemistry 12.2: 163-169 (2001).
Leger et al., "Kringle 5 peptide-albumin conjugates with antimigratory activity." Bioorganic & Medicinal Chemistry Letters 14.4: 841-845 (2004).
Leger et al., "Synthesis and in vitro analysis of atrial natriuretic peptide-albumin conjugates." Bioorganic & Medicinal Chemistry letters 13.20: 3571-3575 (2003).
Lopez-Berenstein, Liposomes in the Therapy of Infectious Disease and Cancer, Lopez—Berestein and Fidler (eds.), Liss, New York, pp. 317-327 (1989).
Maida et al. "The glucagon-like peptide-1 receptor agonist oxyntomodulin enhances β-cell function but does not inhibit gastric emptying in mice." Endocrinology 149.11: 5670-5678 (2008).
Madia et al. "Longevity mutation in SCH9 prevents recombination errors and premature genomic instability in a Werner/Bloom model system", J Cell Biol. Jan. 14, 2008;180(1):67-81.
Meyerovitch et al., "Oral administration of vanadate normalizes blood glucose levels in streptozotocin-treated rats. Characterization and mode of action." Journal of Biological Chemistry 262.14: 6658-6662 (1987).
Moody et al., "A simple free fat cell bioassay for insulin." Hormone and Metabolic Research 6.1: 12-16 (1974).
Mutter et al., "A New Base-Labile Anchoring Group for Polymer-Supported Peptide Synthesis." Helvetica Chimica Acta 67.7: 2009-2016 (1984).
Mutter "Studies on the coupling rates in liquid-phase peptide synthesis using competition experiments", Int J Pept Protein Res. Mar. 1979;13(3):274-7.
Nesher et al. "Reversible pegylation prolongs the hypotensive effect of atrial natriuretic peptide", Bioconjug Chem. Jan. 2008;19(1):342-8.
Nucci et al., "The therapeutic value of poly (ethylene glycol)-modified proteins." Advanced Drug Delivery Reviews 6.2: 133-151 (1991).
O'Kelly et al., "Inactivation of interferon by serum and synovial fluids." Experimental Biology and Medicine 178.3: 407-411 (1985).
Parlevliet et al. "Oxyntomodulin increases insulin secretion but does not affect insulin sensitivity in high-fat-fed C5761/6 mice", Diabetes Jun. 2007 Supplement 1, vol. 56, p. A373.
Parlevliet "Gut Hormones—Novel Tools in the Treatment of Insulin Resistance", thesis 2008, pp. 1-128.

(56) References Cited

OTHER PUBLICATIONS

Parlevliet et al., "Oxyntomodulin ameliorates glucose intolerance in mice fed a high-fat diet." American Journal of Physiology-Endocrinology and Metabolism 294.1: E142-E147 (2008).
Pedersen-Bjergaard et al., "Influence of meal composition on postprandial peripheral plasma concentrations of vasoactive peptides in man." Scandinavian Journal of Clinical & Laboratory Investigation 56.6: 497-503 (1996).
Pellissier, et al. "Oxyntomodulin and glicentin are potent inhibitors of the fed motility pattern in small intestine." Neurogastroenterology & Motility 16.4: 455-463 (2004).
Pellissier et al. "The glycosylation of steroids", Tetrahedron vol. 60, Issue 24, Jun. 7, 2004, pp. 5123-5162.
Peters, "The albumin molecule: its structure and chemical properties." All About Albumin: Biochemistry, Genetics and Medical Applications: 24-54 (1996).
Piehler et al., "Biophysical analysis of the interaction of human ifnar2 expressed in E. coli with IFNa2." Journal of Molecular Biology 289.1: 57-67 (1999).
Piehler et al., "Fast transient cytokine-receptor interactions monitored in real time by reflectometric interference spectroscopy." Analytical biochemistry 289.2: 173-186 (2001).
Pocai, Alessandro. "Unraveling oxyntomodulin, GLP1's enigmatic brother." Journal of Endocrinology 215.3: 335-346 (2012).
Pocai et al. "Glucagon-Like Peptide 1/Glucagon Receptor Dual Agonism Reverses Obesity in Mice", Diabetes, vol. 58, Oct. 2009, pp. 2258-2266.
Pullen et al., "Receptor-binding region of insulin." Nature 259. 5542: 369-373 (1976).
Ramsden "Quantitative Drug Design", Chapter 17.2, F. Choplin Pergamon Press (1990).
Reddy et al., "Use of peginterferon alfa-2a (40 KD)(Pegasys) for the treatment of hepatitis C." Advanced Drug Delivery Reviews 54.4: 571-586 (2002).
Reddy, "Controlled-release, pegylation, liposomal formulations: new mechanisms in the delivery of injectable drugs." Annals of Pharmacotherapy 34.7-8: 915-923 (2000).
Roberts et al., "Chemistry for peptide and protein PEGylation." Advanced Drug Delivery Reviews 54.4: 459-476 (2002).
Rodbell, "Metabolism of Isolated Fat Cells: I. Effects of Hormones on Glucose Metabolism and Lipolysis." Journal of Biological Chemistry 239.2: 375-380 (1964).
Romerio et al., "Interferon-α 2b reduces phosphorylation and activity of MEK and ERK through a Ras/Raf-independent mechanism." British Journal of Cancer 83.4: 532-538 (2000).
Rostaing et al. "Pharmacokinetics of alphaIFN-2b in chronic hepatitis C virus patients undergoing chronic hemodialysis or with normal renal function: clinical implications." Journal of the American Society of Nephrology 9.12: 2344-2348 (1998).
Rubinstein, "Convenient assay for interferons." Journal of Virology 37.2: 755-758 (1981).
Saudek et al., "A preliminary trial of the programmable implantable medication system for insulin delivery." N. Engl. J. Med. 321.9: 574-579 (1989).
Schepp et al., "Exendin-4 and exendin-(9-39) NH2: agonist and antagonist, respectively, at the rat parietal cell receptor for glucagon-like peptide-1-(7-36) NH2." European Journal of Pharmacology: Molecular Pharmacology 269.2: 183-191 (1994).
Schepp et al. "Oxyntomodulin: a cAMP-dependent stimulus of rat parietal cell function via the receptor for glucagon-like peptide-1 (7-36) NH2." Digestion 57.6: 398-405 (1996).
Schwartz et al., "Obesity: keeping hunger at bay." Nature 418.6898: 595-597 (2002).
Schwartz et al., "Central nervous system control of food intake." Nature 404.6778: (2000). 661-671.
Sefton, "Implantable Pumps." CRC Critical Reviews in Biomedical Engineering 14.3: (1987). 201-240.
Shechter et al., "N-[(2-Sulfo)-9-fluorenylmethoxycarbonyl]3-gentamicin C1 Is a Long-Acting Prodrug Derivative." Journal of Medicinal Chemistry 45.19: 4264-4270 (2002).
Shechter et al., "[2-Sulfo-9-fluorenylmethoxycarbonyl]3-exendin-4—a long-acting glucose-lowering prodrug." Biochemical and Biophysical Research Communications 305: 386-391 (2003).
Shechter et al., "Prolonging the half-life of human interferon-α2 in circulation: Design, preparation, and analysis of (2-sulfo-9-fluorenylmethoxycarbonyl) 7-interferon-α2." Proceedings of the National Academy of Sciences 98.3: 1212-1217 (2001).
Shechter et al., "A new approach for prolonging the half-life of peptides, proteins and low-molecular-weight drugs in vivo." Drugs Future 26: 669-676 (2001).
Shechter et al. "Reversible PEGylation of peptide YY3-36 prolongs its inhibition of food intake in mice", FEBS Lett. Apr. 25, 2005;579(11):2439-44.
Shechter et al. "Reversible pegylation of insulin facilitates its prolonged action in vivo", Eur J Pharm Biopharm. Sep. 2008;70(1):19-28.
Stanley et al., "Gastrointestinal satiety signals III. Glucagon-like peptide 1, oxyntomodulin, peptide YY, and pancreatic polypeptide." American Journal of Physiology-Gastrointestinal and Liver Physiology 286.5: G693-G697 (2004).
Studier et al., "Use of T7 RNA polymerase to direct expression of cloned genes." Methods in Enzymology 185: 60-89 (1990).
Supplementary European Search Report for European Patent Application No. 13800444.5 dated Apr. 5, 2016.
Takamatsu et al., "Expression of bacterial chloramphenicol acetyltransferase gene in tobacco plants mediated by TMV-RNA." The EMBO Journal 6.2: 307-311 (1987).
Treat, in "Liposomes in the Therapy of Infectious Disease and Cancer." Lopez-Berestein and Fidler eds., Liss, New York 353-365 (1989).
Tsubery et al. "Prolonging the action of protein and peptide drugs by a novel approach of reversible polyethylene glycol modification", J Biol Chem. Sep. 10, 2004;279(37):38118-24.
Tsushima et al., "Characteristics of solubilized human-somatotropin-binding protein from the liver of pregnant rabbits." Biochemical Journal 187: 479-492 (1980).
Veronese, "Peptide and protein PEGylation: a review of problems and solutions." Biomaterials 22.5: 405-417 (2001).
Vettor et al., "Effects of intravenous neuropeptide Y on insulin secretion and insulin sensitivity in skeletal muscle in normal rats." Diabetologia 41.11: 1361-1367 (1998).
Weissbach and Weissbach, "Methods for Plant Molecular Biology." Selected Methods in Enzymology (USA) Section VIII: 421-463 (1988).
Working et al., "Safety of poly (ethylene glycol) and poly (ethylene glycol) derivatives." in Polyethylene Glycol Chemistry and Biological Applications : 45-57 (1997).
Wynne et al., "Subcutaneous Oxyntomodulin Reduces Body Weight in Overweight and Obese Subjects." Diabetes 54: 2390-2395 (2005).
Zalipsky et al., "New detachable poly (ethylene glycol) conjugates: cysteine-cleavable lipopolymers regenerating natural phospholipid, diacyl phosphatidylethanolamine." Bioconjugate Chemistry 10.5: 703-707 (1999).
Zier et al., "Polyethylene glycol bound benzyl-and fluorenyl derivatives as solubilizing side-chain protecting groups in peptide synthesis." Tetrahedron Letters 35.7: 1039-1042 (1994).
Long Acting Reversible PEGylated Oxyntomdulin-MOD-6030—5$^{th}$ Diabetes Drug Discovery and Development Conference, Apr. 19, 2012. Retrieved from the internet on Feb. 27, 2017 at: <URL:http://www.barchart.com/plmodules/?module=secFilings&filingid=8553514&type=CONVPDF&popup=1&override=1&symbol=PBTH>.
Wellings et al. "[4] Standard FMOC protocols" Methods in enzymology. Dec. 31, 1997;289:44-67.
Pocai, Alessandro, "Action and Therapeutic Potential of Oxyntomodulin", Molecular Metabolism, vol. 3, No. 3, (Jun. 3, 2014) pp. 241-251.
European Search Report for European Patent Application No. 12793107.9 dated Feb. 3, 2015.
Freshney, R.I. Culture of Animal Cells. A Manual of Basic Technique, AR Liss, New York (1983): 3-4.

(56) References Cited

OTHER PUBLICATIONS

Merrifield et al. "9-(2-Sulfo)fluorenylmethyloxycarbonyl chloride, a new reagent for the purification of synthetic peptides", J. Org. Chem., 1978, 43 (25), pp. 4808-4816.

* cited by examiner

A

B

PEGYLATED OXM VARIANTS

CROSS-REFERENCE TO RELATED APPLICATIONS

This application is a National Phase Application of PCT International Application No. PCT/IL2013/050481, International Filing Date Jun. 4, 2013, claiming priority to U.S. Provisional Patent Application No. 61/655,367, filed Jun. 4, 2012, both of which are incorporated by reference herein in their entirety.

FIELD OF INVENTION

A composition which includes oxyntomodulin and polyethylene glycol polymer (PEG polymer) linked via a reversible linker such as 9-fluorenylmethoxycarbonyl (Fmoc) or 2-sulfo-9-fluorenylmethoxycarbonyl (FMS) is disclosed. Pharmaceutical compositions comprising the reverse pegylated oxyntomodulin and methods of using same are also disclosed.

BACKGROUND OF THE INVENTION

The gastrointestinal tract is responsible on synthesize and releasing of many peptide hormones that regulate eating behavior including pancreatic protein (PP), glucagon-like peptide 1 (GLP-1), peptide YY (PYY) and Oxyntomodulin (OXM). OXM arises from a tissue-specific post-transitional processing of proglucagon in the intestine and the CNS. It contains 37 amino acids, including the complete glucagon sequence with a C-terminal basic octapeptide extension that was shown to contribute to the properties of OXM both in-vitro and in-vivo but was not alone sufficient for the effects of the peptide. In response to food ingestion, OXM is secreted by intestinal L cells into the bloodstream proportionally to the meal caloric content.

OXM enhances glucose clearance via stimulation of insulin secretion after both oral and intraperitoneal administration. It also regulates the control of food intake. Intracerebroventricular (ICV) and intranuclear injection of OXM into the paraventricular and arcuate nuclei (ARC) of the hypothalamus inhibits re-feeding in fasting rats. This inhibition has also been demonstrated in freely fed rats at the start of the dark phase. Moreover, peripheral administration of OXM dose-dependently inhibited both fast-induced and dark-phase food intake.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight protein drugs, physiological clearance mechanisms such as renal filtration can make the maintenance of therapeutic levels of a drug unfeasible because of cost or frequency of the required dosing regimen.

Proteins and especially short peptides are susceptible to denaturation or enzymatic degradation in the blood, liver or kidney. Accordingly, proteins typically have short circulatory half-lives of several hours. Because of their low stability, peptide drugs are usually delivered in a sustained frequency so as to maintain an effective plasma concentration of the active peptide. Moreover, since peptide drugs are usually administered by infusion, frequent injection of peptide drugs cause considerable discomfort to a subject. Thus, there is a need for technologies that will prolong the half-lives of therapeutic proteins and peptides while maintaining a high pharmacological efficacy thereof. Such desired peptide drugs should also meet the requirements of enhanced serum stability, high activity and a low probability of inducing an undesired immune response when injected into a subject.

The present invention relates to OXM derivative in which the half-life of the peptide is prolonged utilizing a reversible pegylation technology.

SUMMARY OF THE INVENTION

In one embodiment, the invention relates to a composition consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein said PEG polymer is attached to the amino terminus of said oxyntomodulin via Fmoc or FMS.

In one embodiment, the invention relates to a composition consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein said PEG polymer is attached to a lysine residue on position number twelve ($Lys_{12}$) of said oxyntomodulin's amino acid sequence via Fmoc or FMS.

In another embodiment, the invention relates to a composition consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein said PEG polymer is attached to a lysine residue on position number thirty ($Lys_{30}$) of said oxyntomodulin's amino acid sequence via Fmoc or FMS.

In one embodiment, the invention relates to a method of improving the area under the curve (AUC) of oxyntomodulin, consisting of the step of conjugating a polyethylene glycol polymer (PEG polymer) to the Lysine residue on position number 12 or to the Lysine residue on position number 30 or to the amino terminus of said oxyntomodulin's amino acid sequence via 9-fluorenylmethoxycarbonyl (Fmoc) or 2-sulfo-9-fluorenylmethoxycarbonyl (FMS).

In another embodiment, the invention relates to a method of reducing the dosing frequency of oxyntomodulin, consisting of the step of conjugating a polyethylene glycol polymer (PEG polymer) to the Lysine residue on position number 12 or to the Lysine residue on position number 30 or to the amino terminus of said oxyntomodulin's amino acid sequence via 9-fluorenylmethoxycarbonyl (Fmoc) or 2-sulfo-9-fluorenylmethoxycarbonyl (FMS).

In another embodiment, the invention relates to a method for extending the biological half-life of oxyntomodulin, consisting of the step of conjugating oxyntomodulin, a polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1, wherein said PEG polymer is conjugated to a Lysine residue on position number 12 or to a Lysine residue on position number 30 or to the amino terminus of said oxyntomodulin's amino acid sequence via 9-fluorenylmethoxycarbonyl (Fmoc) or 2-sulfo-9-fluorenylmethoxycarbonyl (FMS).

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
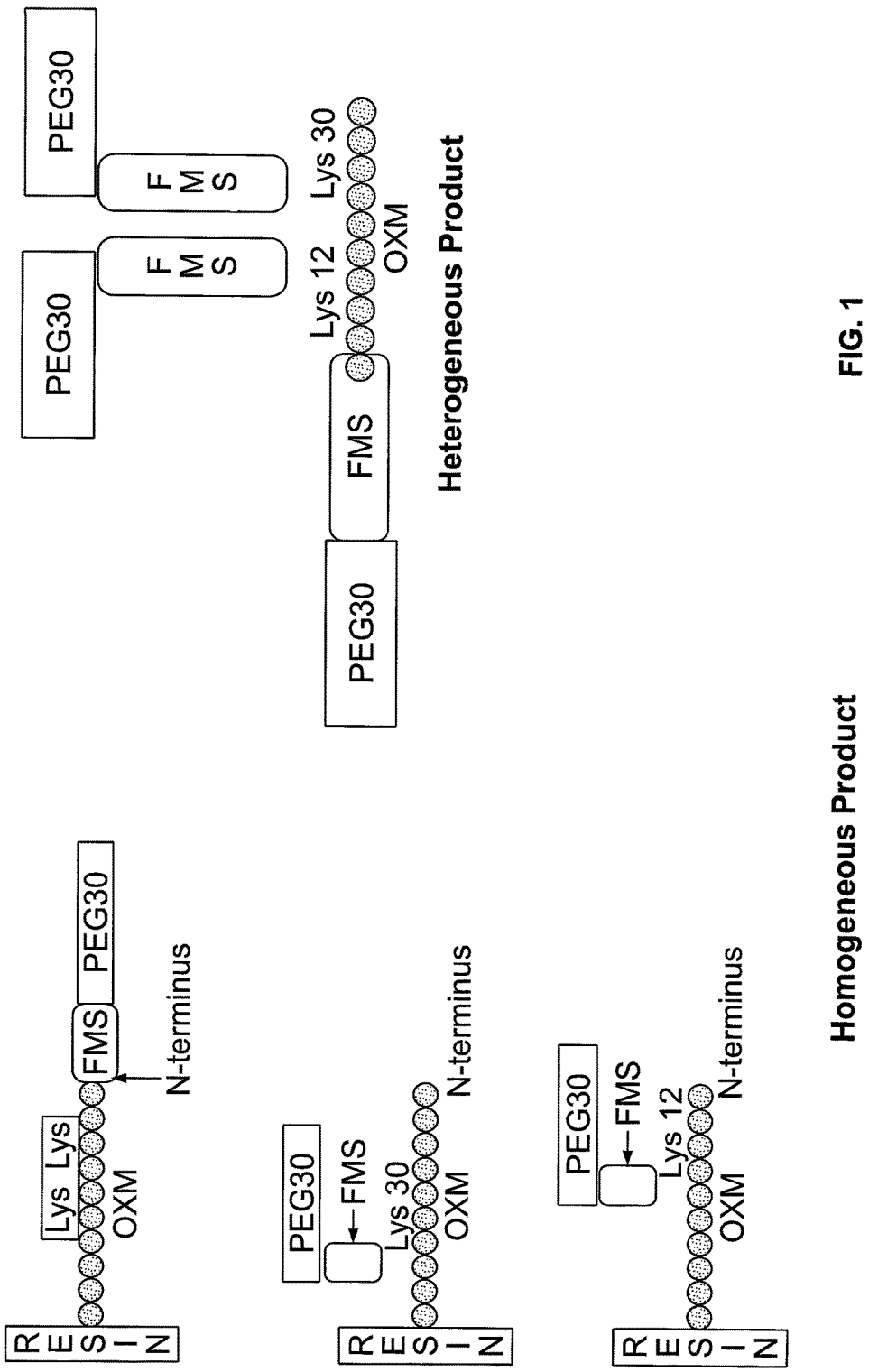
FIG. 1 shows different variants of the PEG-FMS-OXM conjugate produced.
Figure 2:
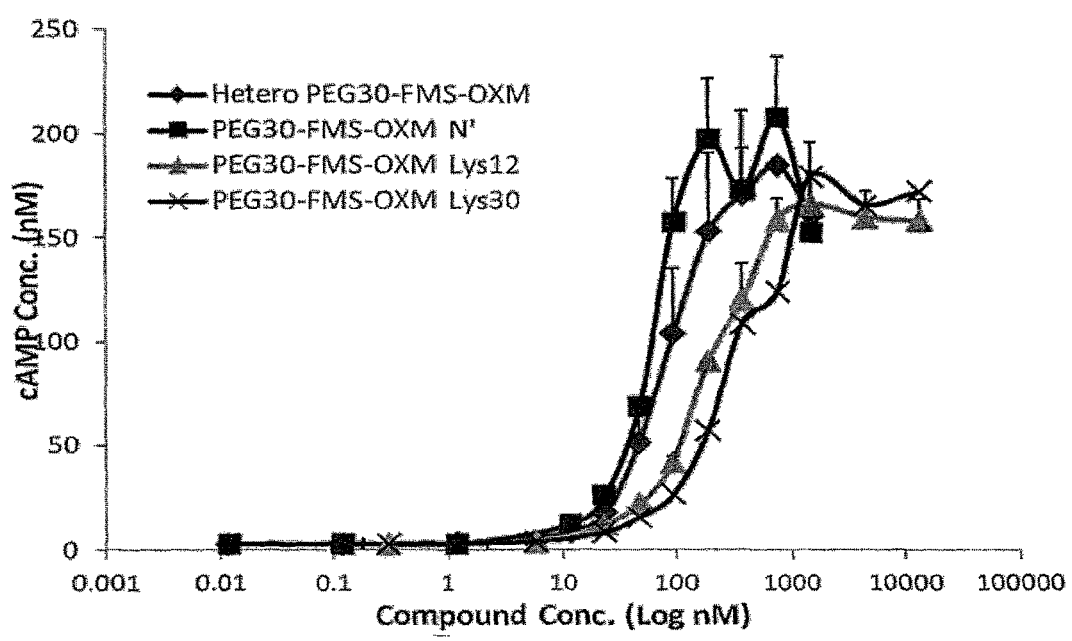
FIG. 2 is a graph showing the in vitro activity (cAMP quantitation) of the heterogeneous $PEG_{30}$-FMS-OXM and the three $PEG_{30}$-FMS-OXM variants (amino, Lys12 and Lys30) when incubated with CHO-K1 cells over-expressing GLP-1 receptor.

Provided herein is a long-acting oxyntomodulin and methods of producing and using same. In one aspect, the invention provides a composition comprising or consisting of a dual GLP-1/Glucagon receptor agonist, a polyethylene glycol polymer (PEG polymer) and 9-fluorenylmethoxycarbonyl (Fmoc) or 2-sulfo-9-fluorenylmethoxycarbonyl (FMS). In another embodiment, the invention provides a composition comprising or consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS). In another embodiment, the PEG polymer is attached to a lysine residue on position number twelve ($Lys_{12}$) of the oxyntomodulin's amino acid sequence via Fmoc or FMS. In one embodiment, a long-acting oxyntomodulin is a composition comprising or consisting of oxyntomodulin and polyethylene glycol polymer (PEG polymer) attached to a lysine residue on position number twelve ($Lys_{12}$) of the oxyntomodulin's amino acid sequence via Fmoc or FMS.

In another aspect, provided herein is a novel method for extending the serum half-life of peptides. This method is based on the reversible attachment of a polyethylene glycol (PEG) chain to the peptide through a chemical linker (called FMS or Fmoc) resulting in the slow release of the native peptide into the bloodstream. The released peptide can then also cross the blood brain barrier to enter the central nervous system (CNS) or any other target organ. In one embodiment, the unique chemical structure of the FMS linker leads to a specific rate of peptide release.

Hence, in another embodiment, provided herein is a method for extending the biological half-life of an OXM peptide. In another embodiment, provided herein is a method for extending the circulating time in a biological fluid of OXM, wherein said circulating time is extended by the slow release of the intact OXM peptide. In another embodiment, extending said biological half-life or said circulating time of said OXM peptide allows said OXM to cross the blood brain barrier and target the CNS. It will be well appreciated by the skilled artisan that the biological fluid may be blood, sera, cerebrospinal fluid (CSF), and the like.

In one embodiment, upon administration of the PEGylated oxyntomodulin composition of the present invention into a subject, the oxyntomodulin is released into a biological fluid in the subject as a result of chemical hydrolysis of said FMS or said Fmoc linker from said composition. In another embodiment, the released oxyntomodulin is intact and regains complete GLP-1 and glucagon receptor binding activity. In another embodiment, chemically hydrolyzing said FMS or said Fmoc extends the circulating time of said OXM peptide in said biological fluid. In another embodiment, extending the circulating time of said OXM allows said OXM to cross the blood brain barrier and target the CNS. In another embodiment, extending the circulating time of said OXM allows said OXM to cross the blood brain barrier and target the hypothalamus. In another embodiment, extending the circulating time of said OXM allows said OXM to cross the blood brain barrier and target the arcuate nucleus.

In one aspect, the amino variant of PEG30-FMS-OXM (designated MOD-6031) is a site directed conjugate comprising OXM and mPEG(30)-SH linked through a bi-functional linker (FMS or Fmoc). In another embodiment, the OXM peptide is connected through its terminal amine of the N-terminus side which reacts with the N-succinimide ester (NHS) group on the linker from one side while mPEG(30)-SH is connected to the maleimide moiety of the FMS linker by its thiol group (see Examples herein). The Lys12 and Lys30 variants are conjugated to the FMS linker through their amine group of Lys residues. In one embodiment, the reversible-pegylation method is utilized herein to generate the long lasting oxyntomodulin (OXM) peptides provided herein (e.g. PEG30-FMS-OXM).

In one embodiment, the terms dual "GLP-1/Glucagon receptor agonist" and "agonist" are used interchangeably herein. In another embodiment, the terms also include any GLP-1/Glucagon receptor agonist known in the art. In another embodiment, the preferred agonist is oxyntomodulin or OXM or a functional variant thereof.

In one embodiment, the term "functional" refers to the ability of the agonist or OXM provided herein to have biological activity, which include but is not limited to, reducing weight, increasing insulin sensitivity, reducing insulin resistance, increasing energy expenditure inducing glucose tolerance, inducing glycemic control, improving cholesterol levels, etc., as further provided herein.

In one embodiment, the invention provides a composition comprising an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein the PEG polymer is attached to a lysine residue on position number thirty ($Lys_{30}$) of said oxyntomodulin amino acid sequence via Fmoc or FMS. In one embodiment, a long-acting oxyntomodulin is a composition comprising or consisting of oxyntomodulin and polyethylene glycol polymer (PEG polymer) attached to a lysine residue on position number twelve ($Lys_{30}$) of the oxyntomodulin amino acid sequence via Fmoc or FMS.

In one embodiment, the invention provides a composition consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein the PEG polymer is attached to a lysine residue on position number thirty ($Lys_{30}$) of said oxyntomodulin's amino acid sequence via Fmoc or FMS. In one embodiment, a long-acting oxyntomodulin is a composition comprising or consisting of oxyntomodulin and polyethylene glycol polymer (PEG polymer) attached to a lysine residue on position number twelve ($Lys_{30}$) of the oxyntomodulin's amino acid sequence via Fmoc or FMS.

In one embodiment, the invention provides a composition comprising an oxyntomodulin, a polyethylene glycol polymer (PEG polymer) and a 9-fluorenylmethoxycarbonyl (Fmoc) or 2-sulfo-9-fluorenylmethoxycarbonyl (FMS), wherein the PEG polymer is attached to the amino terminus of said oxyntomodulin via Fmoc or FMS. In one embodiment, a long-acting oxyntomodulin is a composition comprising or consisting of oxyntomodulin and polyethylene glycol polymer (PEG polymer) attached to the amino terminus of the oxyntomodulin's amino acid sequence via Fmoc or FMS.

In one embodiment, the invention provides composition consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein the PEG polymer is attached to the amino terminus of said oxyntomodulin via Fmoc or FMS. In one embodiment, a long-acting oxyntomodulin is a composition comprising or consisting of oxyntomodulin and polyethylene glycol polymer (PEG polymer) attached to the amino terminus of the oxyntomodulin's amino acid sequence via Fmoc or FMS.

In another embodiment, the present invention provides a composition comprising an oxyntomodulin peptide, and a polyethylene glycol (PEG) polymer conjugated to the oxyntomodulin peptide's lysine amino acid on position twelve (Lys12) or position 30 (Lys30) or on the amino terminus of the oxyntomodulin peptide via a 9-fluorenylmethoxycarbonyl (Fmoc) or 2-sulfo-9-fluorenylmethoxycarbonyl (FMS) linker. In another embodiment, the present invention provides a modified oxyntomodulin peptide consisting of an oxyntomodulin peptide, and a polyethylene glycol (PEG) polymer conjugated to the oxyntomodulin peptide's lysine amino acid on position twelve (Lys12) or position 30 (Lys30) or on the amino terminus of the oxyntomodulin peptide via a 9-fluorenylmethoxycarbonyl (Fmoc) or 2-sulfo-9-fluorenylmethoxycarbonyl (FMS) linker. In another embodiment, the compositions where PEG is attached to oxyntomodulin at Lys12, Lys30 or at the amino terminus are respectively referred to as the "Lys12 variant," the "Lys30 variant" or the "amino variant," of oxyntomodulin. In one embodiment, the term "amino variant" is synonymous with "N-terminal variant", "N' variant" or "N-terminus variant". It is to be understood that a skilled artisan may be guided by the present invention to readily insert lysine residues in a site-specific or random manner throughout the OXM sequence in order to attach a linker (Fmoc or FMS)/PEG conjugate provided herein at these lysine residues. In one embodiment, variants where one or more lysine residues are located in different positions throughout the OXM sequence and are used for conjugating OXM to PEG and cleavable linker (e.g. FMS or Fmoc), are also encompassed in the present invention.

In one embodiment, the present invention provides a composition comprising an oxyntomodulin peptide, and a polyethylene glycol (PEG) polymer conjugated to the oxyntomodulin peptide's lysine amino acid on position twelve (Lys12) and position 30 (Lys30) via a 9-fluorenylmethoxycarbonyl (Fmoc) or 2-sulfo-9-fluorenylmethoxycarbonyl (FMS) linker. In another embodiment, the present invention provides a composition comprising an oxyntomodulin peptide, and a polyethylene glycol (PEG) polymer conjugated to the oxyntomodulin peptide's lysine amino acid on position twelve (Lys12) and on the amino terminus via a 9-fluorenylmethoxycarbonyl (Fmoc) or 2-sulfo-9-fluorenylmethoxycarbonyl (FMS) linker. In another embodiment, the present invention provides a composition comprising an oxyntomodulin peptide, and a polyethylene glycol (PEG) polymer conjugated to the oxyntomodulin peptide's lysine amino acid on position thirty (Lys30) and on the amino terminus via a 9-fluorenylmethoxycarbonyl (Fmoc) or 2-sulfo-9-fluorenylmethoxycarbonyl (FMS) linker.

In another embodiment, a long-acting oxyntomodulin is a pegylated oxyntomodulin. In another embodiment, a long-acting oxyntomodulin is a reversed pegylated oxyntomodulin. In another embodiment, the phrases "long-acting oxyntomodulin," "reversed pegylated oxyntomodulin," "reversible PEGylated OXM," or "a composition comprising or consisting of oxyntomodulin, polyethylene glycol polymer (PEG polymer) and 9-fluorenylmethoxycarbonyl (Fmoc) or 2-sulfo-9-fluorenylmethoxycarbonyl (FMS)" are used interchangeably. In another embodiment, a long-acting oxyntomodulin is OXM linked to PEG via Fmoc or FMS. In another embodiment, the long-acting OXM is linked to Fmoc or FMS via its Lys12 residue, or its Lys30 residue or its amino (N') terminus.

In one embodiment, a long-acting oxyntomodulin of the invention comprises a PEG polymer. In another embodiment, a long-acting oxyntomodulin of the invention comprises a PEG polymer conjugated to the amino terminus of an oxyntomodulin peptide via Fmoc or FMS. In another embodiment, a long-acting oxyntomodulin of the invention comprises a PEG polymer conjugated via Fmoc or FMS to lysine residues 12 or 30 of the oxyntomodulin peptide. In another embodiment, a long-acting oxyntomodulin of the invention comprises a PEG polymer conjugated via Fmoc or FMS to both the amino terminus of an oxyntomodulin peptide and to lysine residues 12 and 30 of oxyntomodulin.

In another embodiment, a long-acting oxyntomodulin is a composition comprising or consisting of oxyntomodulin, polyethylene glycol polymer (PEG polymer) and 9-fluorenylmethoxycarbonyl (Fmoc) or 2-sulfo-9-fluorenylmethoxycarbonyl (FMS) in a molar ratio of 1:0.2-10:0.2-10. In another embodiment, a long-acting oxyntomodulin is a composition comprising or consisting of oxyntomodulin, polyethylene glycol polymer (PEG polymer) and 9-fluorenylmethoxycarbonyl (Fmoc) or 2-sulfo-9-fluorenylmethoxycarbonyl (FMS) in a molar ratio of 1:0.5-2:0.5-2. In another embodiment, a long-acting oxyntomodulin is a composition comprising or consisting of oxyntomodulin, polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1. In another embodiment, a long-acting oxyntomodulin includes a PEG polymer conjugated to the amino terminus of oxyntomodulin via Fmoc or FMS. In another embodiment, the molar ratio of OXM-PEG- and linker is 1:1:1-1:1:3.5. In another embodiment, the molar ratio is 1:1:1-1:1:10.0. In another embodiment, the higher ratio of linker allows for optimized yield of the composition.

In another embodiment, a long-acting oxyntomodulin is linked to PEG via a reversible linker such as, but not limited to, Fmoc and FMS. In another embodiment, Fmoc and FMS are sensitive to bases and are removable under physiological conditions. In another embodiment, a reversible linker is a linker that is sensitive to bases and is removable under physiological conditions. In another embodiment, a reversible linker is a linker that is sensitive to bases and is removable under physiological conditions in the blood, plasma, or lymph. In another embodiment, a reversible linker is a linker that is sensitive to bases and is removable under physiological conditions in a body fluid. In another embodiment, a reversible linker is a linker that is removable in a body fluid having a basic pH. In another embodiment, a linker that is sensitive to bases is cleaved upon exposure to a basic environment thus releasing OXM from the linker and PEG. In another embodiment, a linker that is sensitive to temperature is cleaved upon exposure to specific temperature that allows for such cleavage to take place. In another embodiment, the temperature that enables cleavage of the linker is within the physiological range.

In another embodiment, a reverse pegylated oxyntomodulin is a composition wherein OXM is linked to PEG via a reversible linker. In another embodiment, a reverse pegylated oxyntomodulin releases free OXM upon exposure to a basic environment. In another embodiment, a reverse pegylated oxyntomodulin releases free OXM upon exposure to blood or plasma. In another embodiment, a long-acting oxyntomodulin comprises PEG and oxyntomodulin that are not linked directly to each other, as in standard pegylation procedures, but rather both residues are linked to different positions of Fmoc or FMS which are highly sensitive to bases and are removable under regular physiological conditions. In another embodiment, regular physiological conditions include a physiologic environment such as the blood or plasma.

In another embodiment, the structures and the processes of making Fmoc and FMS are described in U.S. Pat. No. 7,585,837. The disclosure of U.S. Pat. No. 7,585,837 is hereby incorporated by reference in its entirety.

In another embodiment, reverse pegylation renders OXM a long-acting OXM. In another embodiment, long-acting oxyntomodulin is an oxyntomodulin with an extended biological half-life. In another embodiment, reverse pegylation provides protection against degradation of OXM. In another embodiment, reverse pegylation effects the $C_{max}$ of OXM and reduces side effects associated with administration of the composition provided herein. In another embodiment, reverse pegylation extends the $T_{max}$ of OXM. In another embodiment, reverse pegylation extends the circulatory half-live of OXM. In another embodiment, reverse pegylated OXM has improved bioavailability compared to non-modified OXM. In another embodiment, reverse pegylated OXM has improved biological activity compared to non-modified OXM. In another embodiment, reverse pegylation enhances the potency of OXM.

In other embodiments, a reverse pegylated OXM is at least equivalent to the non-modified OXM, in terms of biochemical measures. In other embodiments, a reverse pegylated OXM is at least equivalent to the non-modified OXM, in terms of pharmacological measures. In other embodiments, a reverse pegylated OXM is at least equivalent to the non-modified OXM, in terms of binding capacity (Kd). In other embodiments, a reverse pegylated OXM is at least equivalent to the non-modified OXM, in terms of absorption through the digestive system. In other embodiments, a reverse pegylated OXM is more stable during absorption through the digestive system than non-modified OXM.

In another embodiment, a reverse pegylated OXM exhibits improved blood area under the curve (AUC) levels compared to free OXM. In another embodiment, a reverse pegylated OXM exhibits improved biological activity and blood area under the curve (AUC) levels compared to free OXM. In another embodiment, a reverse pegylated OXM exhibits improved blood retention time ($t_{1/2}$) compared to free OXM. In another embodiment, a reverse pegylated OXM exhibits improved biological activity and blood retention time ($t_{1/2}$) compared to free OXM. In another embodiment, a reverse pegylated OXM exhibits improved blood $C_{max}$ levels compared to free OXM, where in another embodiment it results in a slower release process that reduces side effects associated with administration of the reverse pegylated compositions provided herein. In another embodiment, a reverse pegylated OXM exhibits improved biological activity and blood $C_{max}$ levels compared to free OXM. In another embodiment, provided herein a method of improving OXM's AUC, $C_{max}$, $t_{1/2}$, biological activity, or any combination thereof comprising or consisting of the step of conjugating a polyethylene glycol polymer (PEG polymer) to the amino terminus of free OXM via 9-fluorenylmethoxycarbonyl (Fmoc) or 2-sulfo-9-fluorenylmethoxycarbonyl (FMS).

In another embodiment, improvement of OXM's AUC, $C_{max}$, $t_{1/2}$, biological activity, or any combination thereof by conjugating a polyethylene glycol polymer (PEG polymer) to the amino terminus of free OXM via 9-fluorenylmethoxycarbonyl (Fmoc) or 2-sulfo-9-fluorenylmethoxycarbonyl (FMS) enables the reduction in dosing frequency of OXM. In another embodiment, provided herein a method for reducing a dosing frequency of OXM, comprising or consisting of the step of conjugating a polyethylene glycol polymer (PEG polymer) to the amino terminus or lysine residues of OXM via 9-fluorenylmethoxycarbonyl (Fmoc) or 2-sulfo-9-fluorenylmethoxycarbonyl (FMS). In another embodiment, reverse pegylation of OXM is advantageous in permitting lower dosages to be used.

In another embodiment, OXM comprises the amino acid sequence of SEQ ID NO: 1. In another embodiment, OXM consists of the amino acid sequence of SEQ ID NO: 1. In another embodiment, SEQ ID NO: 1 comprises or consists of the following amino acid (AA) sequence: HSQGTFTSDYSKYLDSRRAQDFVQWLMNTKRNRNNIA (SEQ ID NO: 1). In another embodiment, OXM comprises or consists of the amino acid sequence depicted in CAS No. 62340-29-8.

In another embodiment, OXM is human OXM or any mammal OXM. In another embodiment, OXM is also referred to as glucagon-37 or bioactive enteroglucagon. In another embodiment, OXM is a dual GLP-1/Glucagon receptor agonist. In another embodiment, OXM is a biologically active fragment of OXM. In another embodiment, biologically active OXM extends from amino acid 30 to amino acid 37 of SEQ ID NO: 1. In another embodiment, biologically active OXM extends from amino acid 19 to amino acid 37 of SEQ ID NO: 1. In another embodiment, OXM of the invention corresponds to an octapeptide from which the two C-terminal amino acids are deleted. In another embodiment, OXM of the invention corresponds to any fragment of SEQ ID NO: 1 which retains OXM activity as provided herein.

In one embodiment, OXM refers to a peptide homologue of the peptide of SEQ ID NO: 1. In one embodiment, OXM amino acid sequence of the present invention is at least 50% homologous to the OXM sequence set forth in SEQ ID NO: 1 as determined using BlastP software of the National Center of Biotechnology Information (NCBI) using default parameters. In one embodiment, OXM amino acid sequence of the present invention is at least 60% homologous to the OXM sequence set forth in SEQ ID NO: 1 as determined using BlastP software of the NCBI using default parameters. In one embodiment, OXM amino acid sequence of the present invention is at least 70% homologous to the OXM sequence set forth in SEQ ID NO: 1 as determined using BlastP software of the NCBI using default parameters. In one embodiment, OXM amino acid sequence of the present invention is at least 80% homologous to the OXM sequence set forth in SEQ ID NO: 1 as determined using BlastP software of the NCBI using default parameters. In one embodiment, OXM amino acid sequence of the present invention is at least 90% homologous to the OXM sequence set forth in SEQ ID NO: 1 as determined using BlastP software of the NCBI using default parameters. In one embodiment, OXM amino acid sequence of the present invention is at least 95% homologous to the OXM sequence set forth in SEQ ID NO: 1 as determined using BlastP software of the NCBI using default parameters.

In one embodiment, the long-acting OXM of the invention maintains the biological activity of unmodified OXM. In another embodiment, the long-acting OXM of the invention comprising OXM biological activity. In another embodiment, the biological activity of a long-acting OXM of the invention comprises reducing digestive secretions. In another embodiment, the biological activity of a long-acting OXM of the invention comprises reducing and delaying gastric emptying. In another embodiment, the biological activity of a long-acting OXM of the invention comprises the inhibition of the fed motility pattern in the small intestine. In another embodiment, the biological activity of a long-acting OXM of the invention comprises the inhibition of acid secretion stimulated by pentagastrin. In another embodiment, the biological activity of a long-acting OXM of the invention comprises an increase of gastric somatostatin release. In another embodiment, the biological activity of a long-acting OXM of the invention comprises potentiating the effects of peptide YY. In another embodiment, the biological activity of a long-acting OXM of the invention comprises the inhibition of ghrelin release. In another embodiment, the biological activity of a long-acting OXM of the invention comprises the stimulation of aminopyrine accumulation and cAMP production. In another embodiment, the biological activity of a long-acting OXM of the invention comprises binding the GLP-1 receptor. In another embodiment, the biological activity of a long-acting OXM of the invention comprises binding the Glucagon receptor. In another embodiment, the biological activity of a long-acting OXM of the invention comprises stimulating H+ production by activating the adenylate cyclase. In another embodiment, the biological activity of a long-acting OXM of the invention comprises inhibiting histamine-stimulated gastric acid secretion. In another embodiment, the biological activity of a long-acting OXM of the invention comprises inhibiting food intake. In another embodiment, the biological activity of a long-acting OXM of the invention comprises stimulating insulin release. In another embodiment, the biological activity of a long-acting OXM of the invention comprises inhibiting exocrine pancreatic secretion. In another embodiment, the biological activity of a long-acting OXM of the invention comprises increasing insulin sensitivity. In another embodiment, the biological activity of a long-acting OXM of the invention comprises reducing glucose levels.

In one embodiment, the present invention further provides a method for extending the biological half-life of oxyntomodulin, consisting of the step of conjugating oxyntomodulin, a polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1, wherein, in another embodiment, the PEG polymer is conjugated to a Lysine residue on position number 12 or to a Lysine residue on position number 30 or to the amino terminus of the oxyntomodulin's amino acid sequence via 9-fluorenylmethoxycarbonyl (Fmoc) or 2-sulfo-9-fluorenylmethoxycarbonyl (FMS).

In another embodiment, the invention relates to a method for extending the biological half-life of oxyntomodulin, consisting of the step of conjugating oxyntomodulin, a polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1, wherein said PEG polymer is conjugated to a Lysine residue on position number 12 of the oxyntomodulin's amino acid sequence via 9-fluorenylmethoxycarbonyl (Fmoc) or 2-sulfo-9-fluorenylmethoxycarbonyl (FMS).

In another embodiment, the invention relates to a method for extending the biological half-life of oxyntomodulin, consisting of the step of conjugating oxyntomodulin, a polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1, wherein said PEG polymer is conjugated to a Lysine residue on position number 30 of said oxyntomodulin's amino acid sequence via 9-fluorenylmethoxycarbonyl (Fmoc) or 2-sulfo-9-fluorenylmethoxycarbonyl (FMS).

In another embodiment, the invention relates to a method for extending the biological half-life of oxyntomodulin, consisting of the step of conjugating oxyntomodulin, a polyethylene glycol polymer (PEG polymer) and 9-fluorenylmethoxycarbonyl (Fmoc) or 2-sulfo-9-fluorenylmethoxycarbonyl (FMS) in a molar ratio of 1:1:1, wherein said PEG polymer is conjugated to the amino terminus of said oxyntomodulin's amino acid sequence via 9-fluorenylmethoxycarbonyl (Fmoc) or 2-sulfo-9-fluorenylmethoxycarbonyl (FMS).

In another embodiment, the molar ratio of OXM-PEG- and linker is 1:1:1-1:1:3.5. In another embodiment, the molar ratio is 1:1:1-1:1:10.0. In another embodiment, the higher ratio of linker allows for optimized yield of the composition.

In one embodiment, the invention relates to a method of improving the area under the curve (AUC) of oxyntomodulin, consisting of the step of conjugating a polyethylene glycol polymer (PEG polymer) to the Lysine residue on position number 12 or to the Lysine residue on position number 30 or to the amino terminus of the oxyntomodulin's amino acid sequence via 9-fluorenylmethoxycarbonyl (Fmoc) or 2-sulfo-9-fluorenylmethoxycarbonyl (FMS).

In another embodiment, the invention relates to a method of improving the area under the curve (AUC) of oxyntomodulin, consisting of the step of conjugating a polyethylene glycol polymer (PEG polymer) to the Lysine residue on position number 12 of the oxyntomodulin's amino acid sequence via 9-fluorenylmethoxycarbonyl (Fmoc) or 2-sulfo-9-fluorenylmethoxycarbonyl (FMS).

In one embodiment, the invention relates to a method of improving the area under the curve (AUC) of oxyntomodulin, consisting of the step of conjugating a polyethylene glycol polymer (PEG polymer) to the Lysine residue on position number 30 of the oxyntomodulin's amino acid sequence via 9-fluorenylmethoxycarbonyl (Fmoc) or 2-sulfo-9-fluorenylmethoxycarbonyl (FMS).

In one embodiment, the invention relates to a method of improving the area under the curve (AUC) of oxyntomodulin, consisting of the step of conjugating a polyethylene glycol polymer (PEG polymer) to the amino terminus of the oxyntomodulin's amino acid sequence via 9-fluorenylmethoxycarbonyl (Fmoc) or 2-sulfo-9-fluorenylmethoxycarbonyl (FMS).

In one aspect, provided herein is a method of reducing the dosing frequency of oxyntomodulin, consisting of the step of conjugating a polyethylene glycol polymer (PEG polymer) to the Lysine residue on position number 12 or to the Lysine residue on position number 30 or to the amino terminus of the oxyntomodulis amino acid sequence via 9-fluorenylmethoxycarbonyl (Fmoc) or 2-sulfo-9-fluorenylmethoxycarbonyl (FMS).

In another aspect, provided herein is a method of reducing the dosing frequency of oxyntomodulin, consisting of the step of conjugating a polyethylene glycol polymer (PEG polymer) to the Lysine residue on position number 12 of the oxyntomodulis amino acid sequence via 9-fluorenylmethoxycarbonyl (Fmoc) or 2-sulfo-9-fluorenylmethoxycarbonyl (FMS).

In another aspect, provided herein is a method of reducing the dosing frequency of oxyntomodulin, consisting of the step of conjugating a polyethylene glycol polymer (PEG polymer) to the Lysine residue on position number 30 of the oxyntomodulis amino acid sequence via 9-fluorenylmethoxycarbonyl (Fmoc) or 2-sulfo-9-fluorenylmethoxycarbonyl (FMS).

In another aspect, provided herein is a method of reducing the dosing frequency of oxyntomodulin, consisting of the step of conjugating a polyethylene glycol polymer (PEG polymer) to the amino terminus of the oxyntomodulis amino acid sequence via 9-fluorenylmethoxycarbonyl (Fmoc) or 2-sulfo-9-fluorenylmethoxycarbonyl (FMS).

In another embodiment, the present invention further provides a method for reducing food intake, in a subject, comprising the step of administering to the subject a compositing consisting of oxyntomodulin conjugated to polyethylene glycol polymer (PEG polymer) via a flexible linker, wherein said flexible linker is 9-fluorenylmethoxycarbonyl (Fmoc) or 2-sulfo-9-fluorenylmethoxycarbonyl (FMS), and wherein said PEG polymer is conjugated to a Lysine residue on position number 12 or to a Lysine residue on position number 30 or to the amino terminus of the oxyntomodulin's amino acid sequence via the Fmoc or the FMS.

In another embodiment, the present invention further provides a method for reducing body weight in a subject, comprising the step of administering to the subject a compositing consisting of oxyntomodulin conjugated to polyethylene glycol polymer (PEG polymer) via a flexible linker, wherein said flexible linker is 9-fluorenylmethoxycarbonyl (Fmoc) or 2-sulfo-9-fluorenylmethoxycarbonyl (FMS), and wherein said PEG polymer is conjugated to a Lysine residue on position number 12 or to a Lysine residue on position number 30 or to the amino terminus of the oxyntomodulin's amino acid sequence via the Fmoc or the FMS.

In another embodiment, the present invention further provides a method for inducing glycemic control in a subject, comprising the step of administering to the subject a compositing consisting of oxyntomodulin conjugated to polyethylene glycol polymer (PEG polymer) via a flexible linker, wherein said flexible linker is 9-fluorenylmethoxycarbonyl (Fmoc) or 2-sulfo-9-fluorenylmethoxycarbonyl (FMS), and wherein said PEG polymer is conjugated to a Lysine residue on position number 12 or to a Lysine residue on position number 30 or to the amino terminus of the oxyntomodulin's amino acid sequence via the Fmoc or the FMS.

The amino variant provided herein unexpectedly achieves reduced food intake, weight control and glycemic control, as exemplified herein (see Example 5). In one embodiment, the PEG modification of the OXM peptide provided herein unexpectedly does not interfere with OXM function.

In another embodiment, the present invention provides a method for improving cholesterol levels in a subject, comprising the step of administering to the subject an effective amount of a composition provided herein. In another embodiment, improving cholesterol levels comprises reducing LDL cholesterol while increasing HDL cholesterol in a subject. In another embodiment, LDL cholesterol levels are reduced to below 200 mg/dL, but above 0 mg/dL. In another embodiment, LDL cholesterol levels are reduced to about 100-129 mg/dL. In another embodiment, LDL cholesterol levels are reduced to below 100 mg/dL, but above 0 mg/dL. In another embodiment, LDL cholesterol levels are reduced to below 70 mg/dL, but above 0 mg/dL. In another embodiment, LDL cholesterol levels are reduced to below 5.2 mmol/L, but above 0 mmol/L. In another embodiment, LDL cholesterol levels are reduced to about 2.6 to 3.3 mmol/L. In another embodiment, LDL cholesterol levels are reduced to below 2.6 mmol/L, but above 0 mmol/L. In another embodiment, LDL cholesterol levels are reduced to below 1.8 mmol/L, but above 0 mmol/L.

In another embodiment, the present invention further provides a method for reducing insulin resistance in a subject, comprising the step of administering to the subject an effective amount of a composition provided herein.

In another embodiment, the biological activity of a long-acting OXM of the invention comprises inhibiting pancreatic secretion through a vagal neural indirect mechanism. In another embodiment, the biological activity of a long-acting OXM of the invention comprises reducing hydromineral transport through the small intestine. In another embodiment, the biological activity of a long-acting OXM of the invention comprises stimulating glucose uptake. In another embodiment, the biological activity of a long-acting OXM of the invention comprises controlling/stimulating somatostatin secretion. In another embodiment, the biological activity of a long-acting OXM of the invention comprises reduction in both food intake and body weight gain. In another embodiment, the biological activity of a long-acting OXM of the invention comprises reduction in adiposity. In another embodiment, the biological activity of a long-acting OXM of the invention comprises appetite suppression. In another embodiment, the biological activity of a long-acting OXM of the invention comprises induction of anorexia. In another embodiment, the biological activity of a long-acting OXM of the invention comprises reducing body weight in overweight and obese subjects. In another embodiment, the biological activity of a long-acting OXM of the invention comprises inducing changes in the levels of the adipose hormones leptin and adiponectin. In another embodiment, the biological activity of a long-acting OXM of the invention comprises increasing energy expenditure in addition to decreasing energy intake in overweight and obese subjects.

In another embodiment, a PEG polymer is attached to the amino terminus or lysine residue of oxyntomodulin via Fmoc or FMS. In another embodiment, the terms "attached" and "linked" are use interchangeably. In another embodiment, the PEG polymer is linked to the α-amino side chain of OXM. In another embodiment, the PEG polymer is linked to the ε-amino side chain of OXM. In another embodiment, the PEG polymer is linked to one or more ε-amino side chain of OXM. In another embodiment, the PEG polymer comprises a sulfhydryl moiety.

In another embodiment, PEG is linear. In another embodiment, PEG is branched. In another embodiment, PEG has a molecular weight in the range of 200 to 200,000 Da. In another embodiment, PEG has a molecular weight in the range of 5,000 to 80,000 Da. In another embodiment, PEG has a molecular weight in the range of 5,000 to 40,000 Da. In another embodiment, PEG has a molecular weight in the range of 20,000 Da to 40,000 Da.

In another embodiment, a long-acting OXM is prepared using PEGylating agents, meaning any PEG derivative which is capable of reacting with a functional group such as, but not limited to, $NH_2$, OH, SH, COOH, CHO, —N=C=O, —N=C=S, —$SO_2$Cl, —$SO_2$CH=$CH_2$, —$PO_2$Cl, —($CH_2$)xHal, present at the fluorene ring of the Fmoc or FMS moiety. In another embodiment, the PEGylating agent is usually used in its mono-methoxylated form where only one hydroxyl group at one terminus of the PEG molecule is available for conjugation. In another embodiment, a bifunctional form of PEG where both termini are available for conjugation may be used if, for example, it is desired to obtain a conjugate with two peptide or protein residues covalently attached to a single PEG moiety.

In another embodiment, branched PEGs are represented as $R(PEG-OH)_m$ in which R represents a central core moiety such as pentaerythritol or glycerol, and m represents the number of branching arms. The number of branching arms (m) can range from three to a hundred or more. In another embodiment, the hydroxyl groups are subject to chemical modification. In another embodiment, branched PEG molecules are described in U.S. Pat. Nos. 6,113,906, 5,919,455, 5,643,575, and 5,681,567, which are hereby incorporated by reference in their entirety.

In another embodiment, the present invention provides OXM with a PEG moiety which is not attached directly to the OXM, as in the standard pegylation procedure, but rather the PEG moiety is attached through a linker such as Fmoc or FMS. In another embodiment, the linker is highly sensitive to bases and is removable under mild basic conditions. In another embodiment, OXM connected to PEG via Fmoc or FMS is equivalently active to the free OXM. In another embodiment, OXM connected to PEG via Fmoc or FMS is more active than the free OXM. In another embodiment, OXM connected to PEG via Fmoc or FMS comprises different activity than the free OXM. In another embodiment, OXM connected to PEG via Fmoc or FMS unlike the free OXM, has no central nervous system activity. In another embodiment, OXM connected to PEG via Fmoc or FMS unlike the free OXM, can not enter the brain through the blood brain barrier. In another embodiment, OXM connected to PEG via Fmoc or FMS comprises extended circulation half-life compared to the free OXM. In another embodiment, OXM connected to PEG via Fmoc or FMS loses its PEG moiety together with the Fmoc or FMS moiety thus recovering the free OXM.

In another embodiment, the present invention provides a compound of the formula: $(X)n-Y$, wherein Y is a moiety of OXM bearing a free amino, carboxyl, or hydroxyl and X is a radical of formula (i):

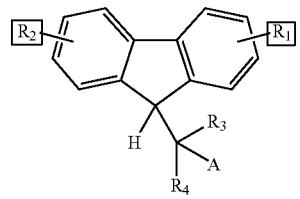

In another embodiment, $R_1$ is a radical containing a protein or polymer carrier moiety; polyethylene glycol (PEG) moiety; $R_2$ is selected from the group consisting of hydrogen, alkyl, alkoxy, alkoxyalkyl, aryl, alkaryl, aralkyl, halogen, nitro, —$SO_3$H, —$SO_2$NHR, amino, ammonium, carboxyl, $PO_3H.sub.2$, and $OPO_3H_2$; R is selected from the group consisting of hydrogen, alkyl and aryl; $R_3$ and $R_4$, the same or different, are each selected from the group consisting of hydrogen, alkyl and aryl; A is a covalent bond when the radical is linked to an amino or hydroxyl group of the OXM-Y; n is an integer of at least one, and pharmaceutically acceptable salts thereof.

In another embodiment, the terms "alkyl", "alkoxy", "alkoxyalkyl", "aryl", "alkaryl" and "aralkyl" are used to denote alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In another embodiment, $R_2$, $R_3$ and $R_4$ are each hydrogen and A is —OCO—, namely the 9-fluorenylmethoxycarbonyl radical (hereinafter "Fmoc"). In another embodiment, R is —$SO_3$H at position 2 of the fluorene ring, $R_3$ and $R_4$ are each hydrogen, and A is —OCO—, namely the 2-sulfo-9-fluorenylmethoxycarbonyl radical (hereinafter "FMS").

In another embodiment, pegylation of OXM and preparation of the (PEG-Fmoc)n-OXM or (PEG-FMS)n-OXM conjugates includes attaching MAL-FMS-NHS or MAL-Fmoc-NHS to the amine component of OXM, thus obtaining a MAL-FMS-OXM or MAL-Fmoc-OXM conjugate, and then substituting PEG-SH for the maleimide moiety, producing the (PEG-FMS)n-OXM or (PEG-Fmoc)n-OXM conjugate, respectively.

In another embodiment, pegylation of OXM includes reacting MAL-FMS-NHS or MAL-Fmoc-NHS with PEG-SH, thus forming a PEG-FMS-NHS or PEG-Fmoc-NHS conjugate, and then reacting it with the amine component of OXM resulting in the desired (PEG-FMS)n-OXM or (PEG-Fmoc)n-OXM conjugate, respectively. In another embodiment, pegylation of peptides/proteins such as OXM are described in U.S. Pat. No. 7,585,837, which is incorporated herein by reference in its entirety. In another embodiment, reverse-pegylation of peptides/proteins such as OXM with Fmoc or FMS are described in U.S. Pat. No. 7,585,837.

In another embodiment, the phrases "long acting OXM" and "reverse pegylated OXM" are used interchangeably. In another embodiment, reverse pegylated OXM is composed of PEG-FMS-OXM and PEG-Fmoc-OXM herein identified by the formulas: (PEG-FMS)n-OXM or (PEG-Fmoc)n-OXM, wherein n is an integer of at least one, and OXM is linked to the FMS or Fmoc radical through at least one amino group.

In another embodiment, the conjugation of PEG-Fmoc or PEG-FMS to Lys12 or Lys30 or the amino terminus of OXM does not render the OXM inactive.

In one embodiment, the Lys12 variant is more effective at providing weight control than the other variants provided herein. In another embodiment, the Lys30 variant provided herein is more effective at achieving weight control than the other variants provided herein. In another embodiment, the amino variant provided herein is more effective at achieving weight control than the other variants provided herein.

In one embodiment, the Lys12 variant is more effective at achieving chronic glycemic control than the other variants provided herein. In another embodiment, the Lys30 variant provided herein is more effective at achieving chronic glycemic control than the other variants provided herein. In another embodiment, the amino variant provided herein is more effective at achieving glycemic control than the other variants provided herein.

Therapeutic Uses

In another embodiment, PEG-Fmoc-OXM and PEG-FMS-OXM and pharmaceutical compositions comprising them are utilized for the prevention of hyperglycemia, for improving glycemic control, for treatment of diabetes mellitus selected from the group consisting of non-insulin dependent diabetes mellitus (in one embodiment, Type 2 diabetes), insulin-dependent diabetes mellitus (in one embodiment, Type 1 diabetes), and gestational diabetes mellitus, or any combination thereof. In another embodiment, PEG-Fmoc-OXM and PEG-FMS-OXM and pharmaceutical compositions comprising them are utilized for treating Type 2 Diabetes. In another embodiment, the PEG-Fmoc-OXM and PEG-FMS-OXM variants provided herein and pharmaceutical compositions comprising them are utilized for increasing sensitivity to insulin. In another embodiment, the PEG-Fmoc-OXM and PEG-FMS-OXM variants provided herein and pharmaceutical compositions comprising them are utilized for reducing insulin resistance.

In another embodiment, the PEG-Fmoc-OXM and PEG-FMS-OXM variants provided herein and pharmaceutical compositions comprising them are utilized for the suppression of appetite. In another embodiment, the PEG-Fmoc-OXM and PEG-FMS-OXM variants provided herein and pharmaceutical compositions comprising them are utilized for inducing satiety. In another embodiment, the PEG-Fmoc-OXM and PEG-FMS-OXM variants provided herein and pharmaceutical compositions comprising them are utilized for the reduction of body weight. In another embodiment, the PEG-Fmoc-OXM and PEG-FMS-OXM variants provided herein and pharmaceutical compositions comprising them are utilized for the reduction of body fat. In another embodiment, the PEG-Fmoc-OXM and PEG-FMS-OXM variants provided herein and pharmaceutical compositions comprising them are utilized for the reduction of body mass index. In another embodiment, the PEG-Fmoc-OXM and PEG-FMS-OXM variants provided herein and pharmaceutical compositions comprising them are utilized for the reduction of food consumption. In another embodiment, the PEG-Fmoc-OXM and PEG-FMS-OXM variants provided herein and pharmaceutical compositions comprising them are utilized for treating obesity. In another embodiment, the PEG-Fmoc-OXM and PEG-FMS-OXM variants provided herein and pharmaceutical compositions comprising them are utilized for treating diabetes mellitus associated with obesity. In another embodiment, the PEG-Fmoc-OXM and PEG-FMS-OXM variants provided herein and pharmaceutical compositions comprising them are utilized for increasing heart rate. In another embodiment, the PEG-Fmoc-OXM and PEG-FMS-OXM variants provided herein and pharmaceutical compositions comprising them are utilized for increasing the basal metabolic rate (BMR). In another embodiment, the PEG-Fmoc-OXM and PEG-FMS-OXM variants provided herein and pharmaceutical compositions comprising them are utilized for increasing energy expenditure. In another embodiment, the PEG-Fmoc-OXM and PEG-FMS-OXM variants provided herein and pharmaceutical compositions comprising them are utilized for inducing glucose tolerance. In another embodiment, the PEG-Fmoc-OXM and PEG-FMS-OXM variants provided herein and pharmaceutical compositions comprising them are utilized for inducing glycemic control. In one embodiment, glycemic control refers to non-high and/or non-fluctuating blood glucose levels and/or non-high and/or non-fluctuating glycosylated hemoglobin levels.

In another embodiment, the PEG-Fmoc-OXM and PEG-FMS-OXM variants provided herein and pharmaceutical compositions comprising them are utilized for inhibiting weight increase, where in another embodiment, the weight increase is due to fat increase. In another embodiment, the PEG-Fmoc-OXM and PEG-FMS-OXM variants provided herein and pharmaceutical compositions comprising them are utilized for reducing blood glucose levels. In another embodiment, the PEG-Fmoc-OXM and PEG-FMS-OXM variants provided herein and pharmaceutical compositions comprising them are utilized for decreasing caloric intake. In another embodiment, the PEG-Fmoc-OXM and PEG-FMS-OXM variants provided herein and pharmaceutical compositions comprising them are utilized for decreasing appetite. In another embodiment, the PEG-Fmoc-OXM and PEG-FMS-OXM variants provided herein and pharmaceutical compositions comprising them are utilized for weight control. In another embodiment, the PEG-Fmoc-OXM and PEG-FMS-OXM variants provided herein and pharmaceutical compositions comprising them are utilized for inducing or promoting weight loss. In another embodiment, the PEG-Fmoc-OXM and PEG-FMS-OXM variants provided herein and pharmaceutical compositions comprising them are utilized for maintaining any one or more of a desired body weight, a desired Body Mass Index, a desired appearance and good health. In another embodiment, PEG the PEG-Fmoc-OXM and PEG-FMS-OXM variants provided herein and pharmaceutical compositions comprising them are utilized for controlling a lipid profile. In another embodiment, the PEG-Fmoc-OXM and PEG-FMS-OXM variants provided herein and pharmaceutical compositions comprising them are utilized for reducing triglyceride levels. In another embodiment, the PEG-Fmoc-OXM and PEG-FMS-OXM variants provided herein and pharmaceutical compositions comprising them are utilized for reducing glycerol levels. In another embodiment, the PEG-Fmoc-OXM and PEG-FMS-OXM variants provided herein and pharmaceutical compositions comprising them are utilized for increasing adiponectin levels. In another embodiment, the PEG-Fmoc-OXM and PEG-FMS-OXM variants provided herein and pharmaceutical compositions comprising them are utilized for reducing free fatty acid levels.

In one embodiment, the terms "reducing the level of" refers to a reduction of about 1-10% relative to an original, wild-type, normal or control level. In another embodiment, the reduction is of about 11-20%. In another embodiment, the reduction is of about 21-30%. In another embodiment, the reduction is of about 31-40%. In another embodiment, the reduction is of about 41-50%. In another embodiment, the reduction is of about 51-60%. In another embodiment, the reduction is of about 61-70%. In another embodiment, the reduction is of about 71-80%. In another embodiment, the reduction is of about 81-90%. In another embodiment, the reduction is of about 91-95%. In another embodiment, the reduction is of about 96-100%.

In one embodiment, the terms "increasing the level of" or "extending" refers to a increase of about 1-10% relative to an original, wild-type, normal or control level. In another embodiment, the increase is of about 11-20%. In another embodiment, the increase is of about 21-30%. In another embodiment, the increase is of about 31-40%. In another embodiment, the increase is of about 41-50%. In another embodiment, the increase is of about 51-60%. In another embodiment, the increase is of about 61-70%. In another embodiment, the increase is of about 71-80%. In another embodiment, the increase is of about 81-90%. In another embodiment, the increase is of about 91-95%. In another embodiment, the increase is of about 96-100%.

In another embodiment, the PEG-Fmoc-OXM and PEG-FMS-OXM variants provided herein and pharmaceutical compositions comprising them are utilized for reducing cholesterol levels. In one embodiment, the reduction in cholesterol levels is greater than the reduction observed after administration of native OXM. In one embodiment, the PEG-Fmoc-OXM and PEG-FMS-OXM variants provided herein and pharmaceutical compositions comprising them lower cholesterol levels by 60-70%. In another embodiment, the PEG-Fmoc-OXM and PEG-FMS-OXM variants provided herein and pharmaceutical compositions comprising them lower cholesterol levels by 50-100%. In another embodiment, the PEG-Fmoc-OXM and PEG-FMS-OXM variants provided herein and pharmaceutical compositions comprising them lower cholesterol levels by 25-90%. In another embodiment, the PEG-Fmoc-OXM and PEG-FMS-OXM variants provided herein and pharmaceutical compositions comprising them lower cholesterol levels by 50-80%. In another embodiment, the PEG-Fmoc-OXM and PEG-FMS-OXM variants provided herein and pharmaceutical compositions comprising them lower cholesterol levels by 40-90%. In another embodiment, the PEG-Fmoc-OXM and PEG-FMS-OXM variants provided herein and pharmaceutical compositions comprising them are utilized for increasing HDL cholesterol levels.

In one embodiment, the PEG-Fmoc-OXM and PEG-FMS-OXM variants provided herein and pharmaceutical compositions comprising them may be used for the purposes described herein without a significant decrease in effectiveness over the course of administration. In one embodiment, PEG-Fmoc-OXM and PEG-FMS-OXM and pharmaceutical compositions comprising them remains effective for 1 day. In another embodiment, PEG-Fmoc-OXM and PEG-FMS-OXM and pharmaceutical compositions comprising them remains effective for 2-6 days. In one embodiment, the PEG-Fmoc-OXM and PEG-FMS-OXM variants provided herein and pharmaceutical compositions comprising them remains effective for 1 week. In another embodiment, the PEG-Fmoc-OXM and PEG-FMS-OXM variants provided herein and pharmaceutical compositions comprising them remain effective for 2 weeks. In another embodiment, the PEG-Fmoc-OXM and PEG-FMS-OXM variants provided herein and pharmaceutical compositions comprising them remain effective for 3 weeks. In another embodiment, the PEG-Fmoc-OXM and PEG-FMS-OXM variants provided herein and pharmaceutical compositions comprising them remain effective for 4 weeks. In another embodiment, the PEG-Fmoc-OXM and PEG-FMS-OXM variants provided herein and pharmaceutical compositions comprising them remain effective for 6 weeks. In another embodiment, the PEG-Fmoc-OXM and PEG-FMS-OXM variants provided herein and pharmaceutical compositions comprising them remain effective for 2 months. In another embodiment, the PEG-Fmoc-OXM and PEG-FMS-OXM variants provided herein and pharmaceutical compositions comprising them remain effective for 4 months. In another embodiment, the PEG-Fmoc-OXM and PEG-FMS-OXM variants provided herein and pharmaceutical compositions comprising them remain effective for 6 months. In another embodiment, the PEG-Fmoc-OXM and PEG-FMS-OXM variants provided herein and pharmaceutical compositions comprising them remain effective for 1 year or more.

In one embodiment, the PEG-Fmoc-OXM and PEG-FMS-OXM variants provided herein and pharmaceutical compositions comprising them may be used for the purposes described herein and may be effective immediately upon administration of the first dose. In another embodiment, PEG the PEG-Fmoc-OXM and PEG-FMS-OXM variants provided herein and pharmaceutical compositions comprising them are effective after two or more doses have been administered.

In another embodiment, methods of utilizing the PEG-Fmoc-OXM and PEG-FMS-OXM variants provided herein and pharmaceutical compositions comprising them as described hereinabove are applied to a human subject afflicted with a disease or condition that can be alleviated, inhibited, and/or treated by OXM. In another embodiment, methods of utilizing the PEG-Fmoc-OXM and PEG-FMS-OXM variants provided herein and pharmaceutical compositions comprising them as described hereinabove are veterinary methods. In another embodiment, methods of utilizing the PEG-Fmoc-OXM and PEG-FMS-OXM variants provided herein and pharmaceutical compositions comprising them as described hereinabove are applied to animals such as farm animals, pets, and lab animals. Thus, in one embodiment, a subject of the present invention is feline, canine, bovine, porcine, murine, aquine, etc.

In another embodiment, the present invention provides a method of treating or reducing a disease treatable or reducible by OXM or a pharmaceutical formulation comprising the same, in a subject, comprising the step of administering to a subject a therapeutically effective amount of the PEG-Fmoc-OXM and/or PEG-FMS-OXM variants provided herein, thereby treating or reducing a disease treatable or reducible by OXM in a subject.

In another embodiment, OXM, "peptide" or "protein" as used herein encompasses native peptides (either degradation products, synthetically synthesized proteins or recombinant proteins) and peptidomimetics (typically, synthetically synthesized proteins), as well as peptoids and semipeptoids which are protein analogs, which have, in some embodiments, modifications rendering the proteins even more stable while in a body or more capable of penetrating into cells.

In another embodiment, a "PEG-Fmoc-OXM and/or a PEG-FMS-OXM variant" is a PEG-Fmoc-OXM and/or a PEG-FMS-OXM variant whereby either FMS or Fmoc is bound to OXM at Lys12. In another embodiment, the PEG-Fmoc-OXM and/or a PEG-FMS-OXM variant is a PEG-Fmoc-OXM and/or a PEG-FMS-OXM variant wherein either FMS or Fmoc is bound to OXM at Lys30. In another embodiment, the PEG-Fmoc-OXM and/or a PEG-FMS-OXM variant is a PEG-Fmoc-OXM and/or a PEG- FMS-OXM variant whereby either FMS or Fmoc is bound to OXM at the amino terminus.

In another embodiment, modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In another embodiment, peptide bonds (—CO—NH—) within the peptide are substituted. In some embodiments, the peptide bonds are substituted by N-methylated bonds (—N(CH3)-CO—). In another embodiments, the peptide bonds are substituted by ester bonds (—C(R)H—C—O—O—C(R)—N—). In another embodiment, the peptide bonds are substituted by ketomethylen bonds (—CO—CH2-). In another embodiment, the peptide bonds are substituted by α-aza bonds (—NH—N(R)—CO—), wherein R is any alkyl, e.g., methyl, carba bonds (—CH2-NH—). In another embodiments, the peptide bonds are substituted by hydroxyethylene bonds (—CH(OH)—CH2-). In another embodiment, the peptide bonds are substituted by thioamide bonds (—CS—NH—). In some embodiments, the peptide bonds are substituted by olefinic double bonds (—CH=CH—). In another embodiment, the peptide bonds are substituted by retro amide bonds (—NH—CO—). In another embodiment, the peptide bonds are substituted by peptide derivatives (—N(R)—CH2-CO—), wherein R is the "normal" side chain, naturally presented on the carbon atom. In some embodiments, these modifications occur at any of the bonds along the peptide chain and even at several (2-3 bonds) at the same time.

In one embodiment, natural aromatic amino acids of the protein such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In another embodiment, the peptides of the present invention include one or more modified amino acid or one or more non-amino acid monomers (e.g. fatty acid, complex carbohydrates etc).

In comparison to the wild-type OXM, the OXM derivatives or variants of the present invention contain several amino acid substitutions, and/or can be PEGylated or otherwise modified (e.g. recombinantly or chemically).

The OXM provided herein also covers any analogue of the above OXM sequence. Any one or more amino acid residues in the sequence can be independently replaced with a conservative replacement as well known in the art i.e. replacing an amino acid with one of a similar chemical type such as replacing one hydrophobic amino acid with another. Alternatively, non-conservative amino acid mutations can be made that result in an enhanced effect or biological activity of OXM. In one embodiment, the OXM is modified to be resistant to cleavage and inactivation by dipeptidyl peptidase IV (DPP-IV). Derivatives, and variants of OXM and methods of generating the same are disclosed in US Patent Application Publication Nos. 2011/0152182, US Patent Application Publication Nos. 2011/0034374, US Patent Application Publication Nos. 2010/0144617, all of which are incorporated by reference herein.

In one embodiment, the dual GLP-1/Glucagon receptor agonist provided herein can be chemically modified. In another embodiment, the OXM provided herein can be chemically modified. In particular, the amino acid side chains, the amino terminus and/or the carboxy acid terminus of OXM can be modified. For example, the OXM can undergo one or more of alkylation, disulphide formation, metal complexation, acylation, esterification, amidation, nitration, treatment with acid, treatment with base, oxidation or reduction. Methods for carrying out these processes are well known in the art. In particular the OXM is provided as a lower alkyl ester, a lower alkyl amide, a lower dialkyl amide, an acid addition salt, a carboxylate salt or an alkali addition salt thereof. In particular, the amino or carboxylic termini of the OXM may be derivatised by for example, esterification, amidation, acylation, oxidation or reduction. In particular, the carboxylic terminus of the OXM can be derivatised to form an amide moiety.

In one embodiment, "amino acid" or "amino acids" is understood to include the 20 naturally occurring amino acids; those amino acids often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids. It is to be understood that other synthetic or modified amino acids can be also be used.

In one embodiment, the OXM of the present invention are utilized in therapeutics which requires OXM to be in a soluble form. In another embodiment, OXM of the present invention includes one or more non-natural or natural polar amino acid, including, but not limited to, serine and threonine which are capable of increasing protein solubility due to their hydroxyl-containing side chain.

In one embodiment, OXM of present invention is biochemically synthesized such as by using standard solid phase techniques. In another embodiment, these biochemical methods include exclusive solid phase synthesis, partial solid phase synthesis, fragment condensation, or classical solution synthesis.

In one embodiment, solid phase OXM synthesis procedures are well known to one skilled in the art and further described by John Morrow Stewart and Janis Dillaha Young, Solid Phase Protein Syntheses (2nd Ed., Pierce Chemical Company, 1984). In another embodiment, synthetic proteins are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In another embodiment, recombinant protein techniques are used to generate the OXM of the present invention. In some embodiments, recombinant protein techniques are used for the generation of large amounts of the OXM of the present invention. In another embodiment, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In another embodiment, OXM of the present invention is synthesized using a polynucleotide encoding OXM of the present invention. In some embodiments, the polynucleotide encoding OXM of the present invention is ligated into an expression vector, comprising a transcriptional control of a cis-regulatory sequence (e.g., promoter sequence). In some embodiments, the cis-regulatory sequence is suitable for directing constitutive expression of the OXM of the present invention.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the peptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, polynucleotides of the present invention are prepared using PCR techniques, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, a variety of prokaryotic or eukaryotic cells can be used as host-expression systems to express the OXM of the present invention. In another embodiment, these include, but are not limited to, microorganisms, such as bacteria transformed with a recombinant bacteriophage DNA, plasmid DNA or cosmid DNA expression vector containing the protein coding sequence; yeast transformed with recombinant yeast expression vectors containing the protein coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the protein coding sequence.

In one embodiment, non-bacterial expression systems are used (e.g. mammalian expression systems such as CHO cells) to express the OXM of the present invention. In one embodiment, the expression vector used to express polynucleotides of the present invention in mammalian cells is pCI-DHFR vector comprising a CMV promoter and a neomycin resistance gene.

In another embodiment, in bacterial systems of the present invention, a number of expression vectors can be advantageously selected depending upon the use intended for the protein expressed. In one embodiment, large quantities of OXM are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the protein. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric protein.

In one embodiment, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In another embodiment, expression vectors containing regulatory elements from eukaryotic viruses such as retroviruses are used by the present invention. SV40 vectors include pSVT7 and pMT2. In another embodiment, vectors derived from bovine papilloma virus include pBV-1MTHA, and vectors derived from Epstein Bar virus include pHEBO, and p2O5. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In one embodiment, plant expression vectors are used. In one embodiment, the expression of OXM coding sequence is driven by a number of promoters. In another embodiment, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the protein), the expression construct of the present invention can also include sequences engineered to optimize stability, production, purification, yield or activity of the expressed protein.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, transformed cells are cultured under effective conditions, which allow for the expression of high amounts of recombinant OXM. In another embodiment, effective culture conditions include, but are not limited to, effective media, bioreactor, temperature, pH and oxygen conditions that permit protein production. In one embodiment, an effective medium refers to any medium in which a cell is cultured to produce the recombinant OXM of the present invention. In another embodiment, a medium typically includes an aqueous solution having assimilable carbon, nitrogen and phosphate sources, and appropriate salts, minerals, metals and other nutrients, such as vitamins. In one embodiment, cells of the present invention can be cultured in conventional fermentation bioreactors, shake flasks, test tubes, microtiter dishes and petri plates. In another embodiment, culturing is carried out at a temperature, pH and oxygen content appropriate for a recombinant cell. In another embodiment, culturing conditions are within the expertise of one of ordinary skill in the art.

In one embodiment, depending on the vector and host system used for production, resultant OXM of the present invention either remain within the recombinant cell, secreted into the fermentation medium, secreted into a space between two cellular membranes, such as the periplasmic space in *E. coli*; or retained on the outer surface of a cell or viral membrane.

In one embodiment, following a predetermined time in culture, recovery of the recombinant OXM is effected.

In one embodiment, the phrase "recovering the recombinant OXM" used herein refers to collecting the whole fermentation medium containing the OXM and need not imply additional steps of separation or purification.

In one embodiment, OXM of the present invention is purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the protein of the present invention and fused cleavable moiety. In one embodiment, a fusion protein can be designed so that the protein can be readily isolated by affinity chromatography; e.g., by immobilization on a column specific for the cleavable moiety. In one embodiment, a cleavage site is engineered between the protein and the cleavable moiety and the protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)]. In another embodiment, the OXM of the present invention is retrieved in "substantially pure" form. In another embodiment, the phrase "substantially pure" refers to a purity that allows for the effective use of the OXM in the applications described herein.

In one embodiment, the OXM of the present invention can also be synthesized using in vitro expression systems. In one embodiment, in vitro synthesis methods are well known in the art and the components of the system are commercially available.

In another embodiment, in vitro binding activity is ascertained by measuring the ability of native, recombinant and/or reverse pegylated OXM as described herein as well as pharmaceutical compositions comprising the same to treat or ameliorate diseases or conditions such as but not limited to: diabetes mellitus, obesity, eating disorders, metabolic disorders, etc. In another embodiment, in vivo activity is deduced by known measures of the disease that is being treated.

In another embodiment, a dose of OXM peptide of the present invention comprises from 0.005 to 0.1 milligrams/kg in an injectable solution. In another embodiment, the comprises from 0.005 to 0.5 milligrams/kg OXM peptide. In another embodiment, the dose comprises from 0.05 to 0.1 micrograms OXM peptide. In another embodiment, the dose comprises from 0.005 to 0.1 milligrams/kg OXM peptide in an injectable solution.

In another embodiment, a dose of reverse pegylated OXM is administered once a day. In another embodiment, a dose of reverse pegylated OXM is administered once every 36 hours. In another embodiment, a dose of reverse pegylated OXM is administered once every 48 hours. In another embodiment, a dose of reverse pegylated OXM is administered once every 60 hours. In another embodiment, a dose of reverse pegylated OXM is administered once every 72 hours. In another embodiment, a dose of reverse pegylated OXM is administered once every 84 hours. In another embodiment, a dose of reverse pegylated OXM is administered once every 96 hours. In another embodiment, a dose of reverse pegylated OXM is administered once every 5 days. In another embodiment, a dose of reverse pegylated OXM is administered once every 6 days. In another embodiment, a dose of reverse pegylated OXM is administered once every 7 days. In another embodiment, a dose of reverse pegylated OXM is administered once every 8-10 days. In another embodiment, a dose of reverse pegylated OXM is administered once every 10-12 days. In another embodiment, a dose of reverse pegylated OXM is administered once every 12-15 days. In another embodiment, a dose of reverse pegylated OXM is administered once every 15-25 days.

In another embodiment, reverse pegylated OXM of the present invention is administered by an intramuscular (IM) injection, subcutaneous (SC) injection, or intravenous (IV) injection once a week.

In another embodiment, the reverse pegylated OXM of the present invention can be provided to the individual per se. In one embodiment, the reverse pegylated OXM of the present invention can be provided to the individual as part of a pharmaceutical composition where it is mixed with a pharmaceutically acceptable carrier.

In another embodiment, a "pharmaceutical composition" refers to a preparation of long-acting OXN as described herein with other chemical components such as physiologically suitable carriers and excipients. The purpose of a pharmaceutical composition is to facilitate administration of a compound to an organism. In another embodiment, a reverse pegylated OXM is accountable for the biological effect.

In another embodiment, any of the compositions of this invention will comprise at least a reverse pegylated OXM. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In another embodiment, "excipient" refers to an inert substance added to a pharmaceutical composition to further facilitate administration of a long-acting OXN. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration of the peptide of the present invention, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

The present invention also includes reverse pegylated OXM for use in the manufacture of a medicament for administration by a route peripheral to the brain for any of the methods of treatment described above. Examples of peripheral routes include oral, rectal, parenteral e.g. intravenous, intramuscular, or intraperitoneal, mucosal e.g. buccal, sublingual, nasal, subcutaneous or transdermal administration, including administration by inhalation. Preferred dose amounts of OXM for the medicaments are given below.

The present invention provides a pharmaceutical composition comprising reverse pegylated OXM and a pharmaceutically suitable carrier, in a form suitable for oral, rectal, parenteral, e.g. intravenous, intramuscular, or intraperitoneal, mucosal e.g. buccal, sublingual, nasal, subcutaneous or transdermal administration, including administration by inhalation. If in unit dosage form, the dose per unit may be, for example, as described below or as calculated on the basis of the per kg doses given below.

In another embodiment, the preparation is administered in a local rather than systemic manner, for example, via injection of the preparation directly into a specific region of a patient's body. In another embodiment, a reverse pegylated OXM is formulated in an intranasal dosage form. In another embodiment, a reverse pegylated OXM is formulated in an injectable dosage form.

Various embodiments of dosage ranges are contemplated by this invention: the OXM peptide component within of the reverse pegylated OXM composition is administered in a range of 0.01-0.5 milligrams/kg body weight per 3 days (only the weight of the OXM within the reverse pegylated OXM composition is provided as the size of PEG can differ substantially). In another embodiment, the OXM peptide component within of the reverse pegylated OXM composition is administered in a range of 0.01-0.5 milligrams/kg body weight per 7 days. In another embodiment, the OXM peptide component within of the reverse pegylated OXM composition is administered in a range of 0.01-0.5 milligrams/kg body weight per 10 days. In another embodiment, the OXM peptide component within of the reverse pegylated OXM composition is administered in a range of 0.01-0.5 milligrams/kg body weight per 14 days. In another embodiment, unexpectedly, the effective amount of OXM in a reverse pegylated OXM composition is $\frac{1}{4}$-$\frac{1}{10}$ of the effective amount of free OXM. In another embodiment, unexpectedly, reverse pegylation of OXM enables limiting the amount of OXM prescribed to a patient by at least 50% compared with free OXM. In another embodiment, unexpectedly, reverse pegylation of OXM enables limiting the amount of OXM prescribed to a patient by at least 70% compared with free OXM. In another embodiment, unexpectedly, reverse pegylation of OXM enables limiting the amount of OXM prescribed to a patient by at least 75% compared with free OXM. In another embodiment, unexpectedly, reverse pegylation of OXM enables limiting the amount of OXM prescribed to a patient by at least 80% compared with free OXM. In another embodiment, unexpectedly, reverse pegylation of OXM enables limiting the amount of OXM prescribed to a patient by at least 85% compared with free OXM. In another embodiment, unexpectedly, reverse pegylation of OXM enables limiting the amount of OXM prescribed to a patient by at least 90% compared with free OXM.

In another embodiment, the OXM peptide component within of the reverse pegylated OXM composition is administered in a range of 0.01-0.5 milligrams/kg body weight once every 3 days (only the weight of the OXM within the reverse pegylated OXM composition is provided as the size of PEG can differ substantially). In another embodiment, the OXM peptide component within of the reverse pegylated OXM composition is administered in a range of 0.01-0.5 milligrams/kg body weight once every 7 days. In another embodiment, the OXM peptide component within of the reverse pegylated OXM composition is administered in a range of 0.01-0.5 milligrams/kg body weight once every 10 days. In another embodiment, the OXM peptide component within of the reverse pegylated OXM composition is administered in a range of 0.01-0.5 milligrams/kg body weight once every 14 days.

In another embodiment, reverse pegylated OXM compared to free OXM both reduces the effective dosing frequency by at least 2-fold and reduces the effective weekly dose by at least 2-fold, thus limiting the risk of adverse events and increasing compliance with the use of OXM therapy. In another embodiment, reverse pegylated OXM compared to free OXM both reduces the effective dosing frequency by at least 3-fold and reduces the effective weekly dose by at least 3-fold, thus limiting the risk of adverse events and increasing compliance with the use of OXM therapy. In another embodiment, reverse pegylated OXM compared to free OXM both reduces the effective dosing frequency by at least 4-fold and reduces the effective weekly dose by at least 4-fold, thus limiting the risk of adverse events and increasing compliance with the use of OXM therapy. In another embodiment, reverse pegylated OXM compared to free OXM both reduces the effective dosing frequency by at least 5-fold and reduces the effective weekly dose by at least 5-fold, thus limiting the risk of adverse events and increasing compliance with the use of OXM therapy. In another embodiment, reverse pegylated OXM compared to free OXM both reduces the effective dosing frequency by at least 6-fold and reduces the effective weekly dose by at least 6-fold, thus limiting the risk of adverse events and increasing compliance with the use of OXM therapy. In another embodiment, effective dosing frequency and effective weekly dose are based on: (1) the weight of administered OXM component within the reverse pegylated OXM composition; and (2) the weight of administered OXM component within the free OXM (unmodified OXM) composition.

In another embodiment, the methods of the invention include increasing the compliance of patients afflicted with chronic illnesses that are in need of OXM therapy. In another embodiment, the methods of the invention enable reduction in the dosing frequency of OXM by reverse pegylating OXM as described hereinabove. In another embodiment, the methods of the invention include increasing the compliance of patients in need of OXM therapy by reducing the frequency of administration of OXM. In another embodiment, reduction in the frequency of administration of the OXM is achieved thanks to reverse pegylation which render the OXM more stable and more potent. In another embodiment, reduction in the frequency of administration of the OXM is achieved as a result of increasing T1/2 of the OXM. In another embodiment, reduction in the frequency of administration of the OXM is achieved as a result of reducing blood clearance of OXM. In another embodiment, reduction in the frequency of administration of the OXM is achieved as a result of increasing T1/2 of the OXM. In another embodiment, reduction in the frequency of administration of the OXM is achieved as a result of increasing the AUC measure of the OXM.

In another embodiment, a reverse pegylated OXM is administered to a subject once a day. In another embodiment, a reverse pegylated OXM is administered to a subject once every two days. In another embodiment, a reverse pegylated OXM is administered to a subject once every three days. In another embodiment, a reverse pegylated OXM is administered to a subject once every four days. In another embodiment, a reverse pegylated OXM is administered to a subject once every five days. In another embodiment, a reverse pegylated OXM is administered to a subject once every six days. In another embodiment, a reverse pegylated OXM is administered to a subject once every week. In another embodiment, a reverse pegylated OXM is administered to a subject once every 7-14 days. In another embodiment, a reverse pegylated OXM is administered to a subject once every 10-20 days. In another embodiment, a reverse pegylated OXM is administered to a subject once every 5-15 days. In another embodiment, a reverse pegylated OXM is administered to a subject once every 15-30 days.

Oral administration, in one embodiment, comprises a unit dosage form comprising tablets, capsules, lozenges, chewable tablets, suspensions, emulsions and the like. Such unit dosage forms comprise a safe and effective amount of OXM of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the long-acting OXN as known to one skilled in the art.

In another embodiment, compositions for use in the methods of this invention comprise solutions or emulsions, which in another embodiment are aqueous solutions or emulsions comprising a safe and effective amount of the compounds of the present invention and optionally, other compounds, intended for topical intranasal administration. In some embodiments, the compositions comprise from about 0.001% to about 10.0% w/v of a subject compound, more preferably from about 00.1% to about 2.0, which is used for systemic delivery of the compounds by the intranasal route.

In another embodiment, the pharmaceutical compositions are administered by intravenous, intra-arterial, subcutaneous or intramuscular injection of a liquid preparation. In another embodiment, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of OXM into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In another embodiment, formulations for injection are presented in unit dosage form, e.g., in ampoules or in multidose containers with optionally, an added preservative. In another embodiment, compositions are suspensions, solutions or emulsions in oily or aqueous vehicles, and contain formulatory agents such as suspending, stabilizing and/or dispersing agents.

The compositions also comprise, in another embodiment, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In one embodiment, pharmaceutical compositions for parenteral administration include aqueous solutions of the active preparation in water-soluble form. Additionally, suspensions of long acting OXM, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of long acting OXM to allow for the preparation of highly concentrated solutions.

In another embodiment, the active compound can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990).

In one embodiment, long acting OXM is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, pharmaceutical compositions suitable for use in context of the present invention include compositions wherein long acting OXM is contained in an amount effective to achieve the intended purpose. In another embodiments, a therapeutically effective amount means an amount of long acting OXM effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin;

talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In another embodiment, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the long acting OXM as described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a reverse pegylated OXM as described herein is administered via systemic administration. In another embodiment, a reverse pegylated OXM as described herein is administered by intravenous, intramuscular or subcutaneous injection. In another embodiment, a reverse pegylated OXM as described herein is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized reverse pegylated OXM as described in sterile water for injection. In another embodiment, a pharmaceutical composition comprises a lyophilized reverse pegylated OXM as described in sterile PBS for injection. In another embodiment, a pharmaceutical composition comprises a lyophilized reverse pegylated OXM as described in sterile 0.9% NaCl for injection.

In another embodiment, the pharmaceutical composition comprises a reverse pegylated OXM as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a reverse pegylated OXM as described herein and lactobionic acid and an acetate/glycine buffer. In another embodiment, the pharmaceutical composition comprises a reverse pegylated OXM as described herein and amino acids, such as arginine or glutamate that increase the solubility of interferon compositions in water. In another embodiment, the pharmaceutical composition comprises a lyophilized reverse pegylated OXM as described herein and glycine or human serum albumin (HSA), a buffer (eg. acetate) and an isotonic agent (e.g NaCl). In another embodiment, the pharmaceutical composition comprises a lyophilized reverse pegylated OXM as described herein and phosphate buffer, glycine and HSA.

In another embodiment, the pharmaceutical composition comprising a pegylated or reverse pegylated OXM as described herein is stabilized when placed in buffered solutions having a pH between about 4 and 7.2. In another embodiment, the pharmaceutical composition comprising a reverse pegylated OXM as described herein is stabilized with an amino acid as a stabilizing agent and in some cases a salt (if the amino acid does not contain a charged side chain).

In another embodiment, the pharmaceutical composition comprising a reverse pegylated OXM as described herein is a liquid composition comprising a stabilizing agent at between about 0.3% and 5% by weight which is an amino acid.

In another embodiment, the pharmaceutical composition comprising a reverse pegylated OXM as described herein provides dosing accuracy and product safety. In another embodiment, the pharmaceutical composition comprising a reverse pegylated OXM as described herein provides a biologically active, stable liquid formulation for use in injectable applications. In another embodiment, the pharmaceutical composition comprises a non-lyophilized reverse pegylated OXM as described herein.

In another embodiment, the pharmaceutical composition comprising a reverse pegylated OXM as described herein provides a liquid formulation permitting storage for a long period of time in a liquid state facilitating storage and shipping prior to administration.

In another embodiment, the pharmaceutical composition comprising a reverse pegylated OXM as described herein comprises solid lipids as matrix material. In another embodiment, the injectable pharmaceutical composition comprising a reverse pegylated OXM as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser E P 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a reverse pegylated OXM as described herein is in the form of liposomes (J. E. Diederichs and al., Pharm./nd. 56 (1994) 267-275).

In another embodiment, the pharmaceutical composition comprising a reverse pegylated OXM as described herein comprises polymeric microparticles. In another embodiment, the injectable pharmaceutical composition comprising a reverse pegylated OXM as described herein comprises polymeric microparticles. In another embodiment, the pharmaceutical composition comprising a reverse pegylated OXM as described herein comprises nanoparticles. In another embodiment, the pharmaceutical composition comprising a reverse pegylated OXM as described herein comprises liposomes. In another embodiment, the pharmaceutical composition comprising a reverse pegylated OXM as described herein comprises lipid emulsion. In another embodiment, the pharmaceutical composition comprising a reverse pegylated OXM as described herein comprises microspheres. In another embodiment, the pharmaceutical composition comprising a reverse pegylated OXM as described herein comprises lipid nanoparticles. In another embodiment, the pharmaceutical composition comprising a reverse pegylated OXM as described herein comprises lipid nanoparticles comprising amphiphilic lipids. In another embodiment, the pharmaceutical composition comprising a reverse pegylated OXM as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the long acting OXM. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the reverse pegylated OXM of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

PEG30-FMS-OXM Synthesis—Heterogeneous 1.1 Stage 1: OXM Synthesis

Oxyntomodulin was synthesized which consists of the following peptide sequence:
HSQGTFTSDYSKYLDSRRAQDFVQWLMNTKRNRN-NIA (SEQ ID NO: 1)

The peptide was synthesized by the solid phase method employing the Fmoc-strategy throughout the peptide chain assembly (Almac Sciences, Scotland).

The peptide sequence was assembled using the following steps:

1. Capping

The resin was capped using 0.5M acetic anhydride (Fluka) solution in DMF (Rathburn).

2. Deprotection

Fmoc-protecting group was removed from the growing peptide chain using 20% v/v piperidine (Rathburn) solution in DMF (Rathburn).

3. Amino Acid Coupling 0.5M Amino acid (Novabiochem) solution in DMF (Rathburn) was activated using 1M HOBt (Carbosynth) solution in DMF (Rathburn) and 1M DIC (Carbosynth) solution in DMF (Rathburn). 4 equivalents of each amino acid were used per coupling.

The crude peptide is cleaved from the resin and protecting groups removed by stirring in a cocktail of Triisopropylsilane (Fluka), water, dimethylsulphide (Aldrich), ammonium iodide (Aldrich) and TFA (Applied Biosystems) for 4 hours. The crude peptide is collected by precipitation from cold diethyl ether.

Peptide Purification

Crude peptide was dissolved in acetonitrile (Rathburn)/water (MilliQ) (5:95) and loaded onto the preparative HPLC column. The chromatographic parameters are as follows:
Column: Phenomenex Luna C18 250 mm×30, 15 μm, 300A
Mobile Phase A: water+0.1% v/v TFA (Applied Biosystems)
Mobile Phase B: acetonitrile (Rathburn)+0.1% v/v TFA (Applied Biosystems)
UV Detection: 214 or 220 nm
Gradient: 25% B to 31% B over 4 column volumes
Flow rate 43 mL/min Stage 2—Linker Synthesis Scheme 1-Synthesis of MAL-FMS-NHS Linker

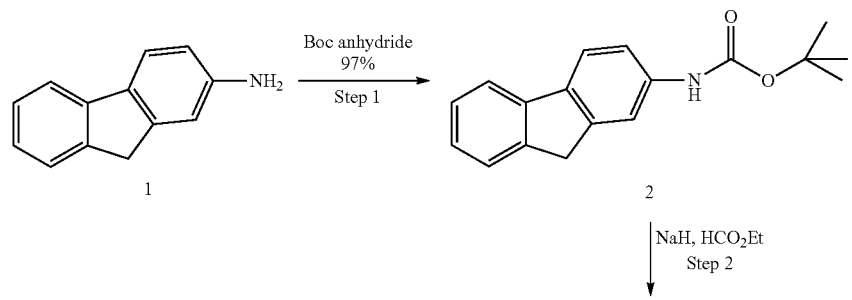

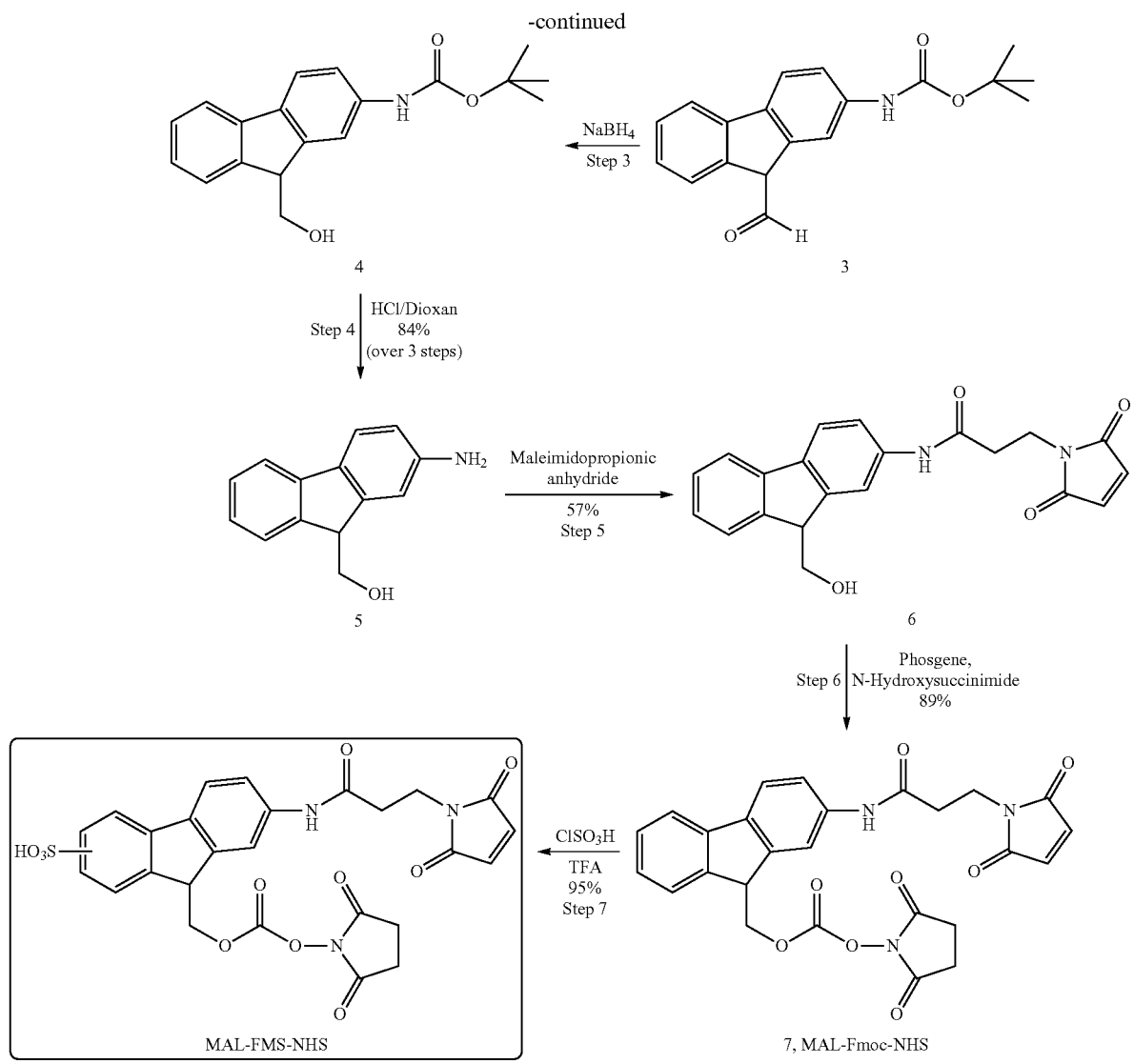

The synthesis of compounds 2-5 is based on the procedures described by Albericio et al. in Synthetic Communication, 2001, 31(2), 225-232.

2-(Boc-amino)fluorene (2):

2-Aminofluorene (18 g, 99 mmol) was suspended in a mixture of dioxane:water (2:1) (200 ml) and 2N NaOH (60 ml) in an ice bath with magnetic stirring. Boc$_2$O (109 mmol, 1.1 eq) was then added and stirring continued at RT. The reaction was monitored by TLC (Rf=0.5, Hex./Ethyl Acetate 2:1) and the pH maintained between 9-10 by addition of 2N NaOH. At reaction completion, the suspension was acidified with 1M KHSO4 to pH=3. The solid was filtered and washed with cold water (50 ml), dioxane-water (2:1) and then azeotroped with toluene twice before using it in the next step.

9-Formyl-2-(Boc-amino)fluorene (3):

In a 3 necked RBF, NaH (60% in oil; 330 mmol, 3.3 eq) was suspended in dry THF (50 ml), a solution of -(Boc-amino)fluorine described in step 2 (28 g; 100 mmol) in dry THF (230 ml) was added dropwise over 20 minutes. A thick yellow slurry was observed and the mixture stirred for 10 minutes at RT under nitrogen. Ethyl formate (20.1 ml, 250 mmol, 2.5 eq) was added dropwise (Caution: gas evolution). The slurry turned to a pale brown solution. The solution was stirred for 20 minutes. The reaction was monitored by TLC (Rf=0.5, Hex./Ethyl acetate 1:1) and when only traces of starting material was observed, it was quenched with iced water (300 ml). The mixture was evaporated under reduce pressure until most of the THF has been removed. The resulting mixture was treated with acetic acid to pH=5. The white precipitate obtained was dissolved in ethyl acetate and the organic layer separated. The aqueous layer was extracted with ethyl acetate and all the organic layer combined and washed with saturated sodium bicarbonate, brine and dried over MgSO$_4$. After filtration and solvent removal a yellow solid was obtained. This material was used in the next step.

9-Hydroxymethyl-2-(Boc-amino)fluorene (4):

Compound 3 from above was suspended in MeOH (200 ml) and sodium borohydride was added portion wise over 15 minutes. The mixture was stirred for 30 minutes (caution: exothermic reaction and gas evolution). The reaction was monitored by TLC (Rf=0.5, Hex./EtOAc 1:1) and was completed. Water (500 ml) was added and the pH adjusted to 5 with acetic acid. The work up involved extraction twice with ethyl acetate, washing the combined organic layers with sodium bicarbonate and brine, drying over MgSO$_4$, filtration and concentration to dryness. The crude obtained was purified by flask chromatography using Heptane/EtOAc (3:1) to give a yellow foam (36 g, 97.5% purity, traces of ethyl acetate and diethyl ether observed in the 1H-NMR).
MAL-Fmoc-NHS (7):

To a clean dry 500 ml RBF with overhead agitation was charged triphosgene (1.58 g, 0.35 eq.) in dry THF (55 ml) to form a solution at ambient. This was cooled to 0° C. with an ice/water bath and a solution of NHS (0.67 g, 0.38 eq) in dry THF (19 ml) added dropwise over 10 minutes under nitrogen at 0° C. The resultant solution was stirred for 30 minutes. A further portion of NHS (1.34 g, 0.77 eq) in dry THF (36 ml) was added dropwise at 0° C. over 10 minutes and stirred for 15 minutes.

Compound 6 (5.5 g, 1 eq), dry THF (55 ml) and pyridine (3.07 ml, 2.5 eq) were stirred together to form a suspension. This was added to the NHS solution in portions a 0-5° C. and then allowed to go to RT by removing the ice bath.

After 20 hours the reaction was stop (starting material still present, if the reaction is pushed to completion a dimmer impurity has been observed).

The reaction mixture was filtered and to the filtrate, 4% brine (200 ml) and EtOAc (200 ml) were added. After separation, the organic layer was washed with 5% citric acid (220 ml) and water (220 ml). The organic layer was then concentrated to give 7.67 g of crude MAL-Fmoc-NHS. The material was purified by column chromatography using a gradient cyclohexane/EtOAc 70:30 to 40:60. The fractions containing product were concentrated under vacuum to give 3.47 g (45%) of MAL-Fmoc-NHS.
MAL-FMS-NHS:

To a solution of MAL-Fmoc-NHS (100 mg, 0.2 mmol) in trifluoroacetic acid (10 ml), chlorosulfonic acid (0.5 ml) was added. After 15 minutes, ice-cold diethyl ether (90 ml) was added and the product precipitated. The material was collected by centrifugation, washed with diethyl ether and dried under vacuum. 41.3 mg (35%) of beige solid was obtained.

Stage 3—Conjugation

Heterogenous conjugation of the 3 amines sites in the OXM peptide (Lys12, Lys30 and amino terminal) performed as "one pot reaction" in which 1 eq from each component: OXM, mPEG-SH and FMS linker as mixed together at Ph 7.2 for 30 min. The reaction stopped by adding acetic acid to reduce PH to 4.
PEG30-FMS-OXM Synthesis—Homogeneous Stage 1: The Spacer MAL-FMS-NHS (FMS) synthesis: as described for the heterogenous conjugate.

Stage 2: Oxyntomodulin (OXM) Synthesis:

N-terminus site directed OXM—as described above for heterogeneous conjugate.

Lys$_{12}$ or Lys$_{30}$ site directed OXM—Using the same strategy except for using Fmoc-Lys(ivDde)-OH in position 12 or 30 of lysine and Boc-His(Boc)-OH as the last amino acid to be coupled.

Stage 3: Homogeneous Conjugation
Coupling FMS to OXM:

MAL-FMS-NHS linker solution (0.746 ml, 10 mg/ml in DMF, 2 eq) was added to OXM resin (1 eq, 200 mg resin, 31.998 μmol/g free amine) DMF was added until resin was just freely mobile and then sonicated for 19 hrs. Resin was washed with DMF and Methanol before drying overnight in vacuum desiccator. The cleavage cocktail contained TFA/TIS/H2O. The cleavage was performed over 3.5 hrs at room temperature. After filtration of the resin, the FMS-OXM was precipitated in cold diethyl ether. 42.1 mg of crude FMS-OXM (36% pure) was obtained at the end of the cleavage stage.
Coupling FMS to Lys$_{12}$ Site Directed OXM:

MAL-FMS-NHS linker solution (10 mg/ml in DMF, 2.5 equiv.) was added to (Lys12)OXM resin (1 equiv.) with addition of DIEA (5 equiv.). DMF was added until resin was just freely mobile and then sonicated overnight. Resin was washed with DMF and Methanol before drying overnight in vacuum desiccator. Cleavage and precipitation as described for N-terminal site directed.
Coupling FMS to Lys$_{30}$ Site Directed OXM:

MAL-FMS-NHS linker (2.5 equiv.) was solubilized in DCM with addition of DIEA (5 equiv.). This linker/DIEA solution was added to (Lys30)OXM resin then sonicated overnight. Resin was washed with DCM and Methanol before drying overnight in vacuum desiccator. Cleavage and precipitation as described for N-terminal site directed.
Purification The resultant crude FMS-OXM was purified in one portion.
Sample diluent: 10% Acetonitrile in water
Column: Luna C18 (2), 100 Å, 250×21.2 mm
Injection flow rate: 9 ml/min
Run flow rate: 9 ml/min
Buffer A: Water (0.1% TFA)
Buffer B: Acetonitrile (0.1% TFA)
Gradient: 10-45% B over 32 mins
Monitoring: 230 nm
Conjugation of PEG30 to FMS-OXM FMS-OXM solution (1 equiv, 15.1 mg in 1.5 ml DMF) was prepared. PEG30 (1 equiv, 9.2 ml of 10 mg/ml in pH 6.5 phosphate buffer) was added to the FMS-OXM solution. The reaction mixture was then stirred for 30 mins at room temperature before adding glacial acetic acid (200 μl) to quench reaction by lowering the pH.

The resultant reaction mixture was then purified using RP-HPLC.
Column: Luna C18 (2), 100 Å, 250×21.2 mm
Injection flow rate: 5 ml/min
Run flow rate: 20 ml/min
Buffer A: Water & 0.1% TFA
Buffer B: Acetonitrile/Water (75:25) & 0.1% TFA
Gradient: 10-65% B over 41 mins
Monitoring: 220, 240, 280 nm
IP Glucose Tolerance Test C57BL/6 male mice were fasted overnight then weighed, and blood glucose levels were measured by tail vein sampling using a handheld glucometer. Mice were IP injected with PEG-SH (vehicle), PEG30-FMS-OXM (Heterogeneous) and the three homogeneous variants of PEG30-FMS-OXM (amino, Lys12 and Lys30). Glucose (1.5 gr/kg) was administrated IP 15 min after test article administration. Blood glucose levels were measured by tail vein sampling at prior to glucose administration and 10, 20, 30, 60, 90, 120 and 180 min after glucose administration using a handheld glucometer.
In-Vitro Characterization of GLP-1 Receptors Activation Activation of GLP-1 receptor was assessed using two different cell lines; HTS163C2 (Millipore) and cAMP Hunter™ CHO-K1 GLP1R (Discoverx), both are over expressing the GLP-1 receptor. The HTS163C2 (Millipore) were seeded in 96 wells half-area white plate (Greiner) at a density of 100,000 cells/ml and incubated for 24 hours at 37° C. The cells were incubated with escalating concentrations of heterogeneous PEG30-FMS-OXM and 3 homogeneous PEG30-FMS-OXM variants (amino, Lys12 and Lys30).

Cells cAMP concentrations were quantified by HTRF assay (Cisbio 62AM4PEB) and EC50 parameter was analyzed by PRISM software. The cAMP Hunter™ CHO-K1 GLP1R secretes cAMP upon binding of the ligand to the receptor. Cells at a density of 500000 cells/ml were seeded in 96 wells plate, and were incubated for 24 h at 37° C. with 5% $CO_2$ Ligands were diluted in diluent contains IBMX and were added in duplicate to the culture wells for 30 min at 37° C. with 5% $CO_2$. The concentration range of PEG30-FMS-OXM was $1.5*10^{-10}$ to $1.2*10^{-6}$ M. Lysis buffer and detector reagents were added to the wells and cAMP concentrations were detected using a chemiluminescent signal. The dose dependent curves were established and the binding affinities (EC50) of various ligands were calculated using PRISM software by applying the best fit dose response model (Four parameters).

In-Vitro Characterization of Glucagon Receptors Activation

Activation of glucagon receptor was assessed using cAMP Hunter™ CHO-K1 GCGR cell-line that over expresses glucagon-receptor. This cell-line secretes cAMP upon binding of the ligand to the glucagon receptor. Cells were seeded at a density of 500000 cells/ml in 96 wells plate, and were incubated for 24 h at 37° C. with 5% $CO_2$ Ligands were diluted in diluent contains IBMX and were added in duplicate to the culture wells for 30 min at 37° C. with 5% $CO_2$. The concentration range of MOD-6031 was $5.8*10^{-11}$ to $2.7*10^{-7}$ M. Lysis buffer and detector reagents were added to the wells and cAMP concentrations were detected using a chemiluminescent signal. The dose dependent curves were established and the binding affinities (EC50) of various ligands were calculated using PRISM software by applying the best fit dose response model (Four parameters).

Obese (Ob/Ob) Mice Model

Study 1: Twenty five male ob/ob mice (male, B6. V-Lep^ob/OlaHsd, 5-6 weeks of age, Harlan) were acclimatized to the facility (10 days) followed by handling protocol whereby animals were handled as if to be dosed but were actually not weighed or dosed (10 days). Subsequently, animals underwent baseline period for 7 days in which they were dosed twice a week with the appropriate vehicle by the subcutaneous route in volume of 20 ml/kg. Body weight, food and water intake were recorded daily, and samples were taken for non-fasting and fasting glucose measurements and non-fasting and fasting insulin measurements. Animals were subsequently allocated into five treatment groups (N=5) based on body weight and glycemic profile. Animals were dosed every four days (days: 1, 5, 9, 13 and 16) as describes in table 1. During the treatment period, food intake, water intake and body weight have been measured and recorded daily, before dosing. Several procedures and sampling have been performed: non-fasting and fasting glucose on days 2, 6, 14 and 17 (on day 17 only non-fasting glucose was measured), fasting and non-fasting insulin (days 2, 6 and 14). Terminal samples on day 19 were analyzed for cholesterol.

TABLE 1

Study design

| Group | Treatment (sc) | Frequency | n |
|---|---|---|---|
| 1 | PEG-SH (142.86 mg/ml) | Days 1, 5, 9, 13 and 16 | 5 |
| 2 | PEG-FMS-OXM Hetero (MOD-6030). 2000 nmol/kg | Days 1, 5, 9, 13 and 16 | 5 |
| 3 | Amino PEG-FMS-OXM 2000 nmol/kg | Days 1, 5, 9, 13 and 16 | 5 |

TABLE 1-continued

Study design

| Group | Treatment (sc) | Frequency | n |
|---|---|---|---|
| 4 | Lys12 PEG-FMS-OXM 2000 nmol/kg | Days 1, 5, 9, 13 and 16 | 5 |
| 5 | Lys30 PEG-FMS-OXM 2000 nmol/kg | Days 1, 5, 9, 13 and 16 | 5 |

Study 2:

One hundred male ob/ob mice (5-6 weeks of age, Charles River) were acclimatized to the facility (3 days) followed by handling protocol whereby animals were handled as if to be dosed but were actually not weighed or dosed (7 days). Subsequently, animals were underwent baseline period for 7 days in which they were dosed twice a week with PEG30-SH vehicle (146 mg/ml) by a subcutaneous route in volume of 20 ml/kg. Body weight, food and water intake were recorded daily. Subsequently animals were allocated into 8 treatment, control and pair fed groups (groups A-H, N=8) (table 2). The pair fed group was pair-fed to the high dose (6000 nmol/kg) group of MOD-6031 and it was given the daily food ration equal to that eaten by its paired counterpart in group D the previous day. 3 additional groups (groups I-K, N=12) were administered with MOD-6031 at 1000, 3000 and 6000 nmol/kg and were used for sampling for PK analysis. PEG-SH vehicle (292 mg/ml), MOD-6031 at 1000, 3000 and 6000 nmol/kg, and the pair fed groups were administered twice a week for 32 days while OXM, Liraglutide® and PBS were administered bid. Body weight, food and water intake were measured daily. Non-fasting and fasting glucose were measured once a week, OGTT were performed on days 2 and 30. Terminal blood samples (day 33) were analyzed for glucose, insulin, Cholesterol, and MOD-6031, PEG-FMS and OXM concentrations. Mice in the PK groups received a single dose of MOD-6031 and blood samples were taken at 4, 8, 24, 36, 48, 72, 96 and 120 h (n=3 per time point) for PK analysis allows to quantify MOD-6031 and its compounds concentrations by LC-MS/MS method.

TABLE 2

Study design

| Group | Treatment (sc) | n | Frequency |
|---|---|---|---|
| A | PEG30-SH Vehicle (292 mg/kg; 20 ml/kg) | 8 | Twice a week on days 1, 4, 8, 11, 15, 18, 22, 25, 29 and 32 |
| B | MOD-6031 1000 nmoles/kg | 8 | |
| C | MOD-6031 3000 nmoles/kg | 8 | |
| D | MOD-6031 6000 nmoles/kg | 8 | |
| E | PEG30-SH Vehicle (292 mg/kg) Pair-Fed to Group D | 8 | |
| F | PBS bid (10 ml/kg) | 8 | b.i.d for 32 days |
| G | OXM 6000 nmol/kg bid (10 ml/kg) | 8 | |
| H | Liraglutide 0.1 mg/kg bid (10 ml/kg) | 8 | |
| I | MOD-6031 1000 nmoles/kg PK group | 12 | Single injection on day 1 |
| J | MOD-6031 3000 nmoles/kg PK group | 12 | |
| K | MOD-6031 6000 nmoles/kg PK group | 12 | |

Results

Example 1

Manufacturing and Development Synthesis

The composition of the PEG-FMS-OXM conjugate depends on its synthesis procedure. Different variants of the PEG-FMS-OXM conjugate were produced (FIG. 1).
Heterogenous Conjugate:

Synthesis of MOD-6030 (PEG$_{30}$-FMS-OXM) was performed as follows: FMS spacer was mixed with OXM and PEG(30)-SH (as one pot reaction). The FMS spacer was coupled to OXM by its NHS activated ester on one side and by PEG-SH connected to the maleimide group on the other side simultaneously. This way, a heterogeneous mixture of PEG-FMS-OXM conjugate is composed of three variants connected by one of the 3 amines of the OXM peptide (N-terminal, Lys$_{12}$ and Lys$_{30}$).
Homogeneous Conjugate:

The conjugation procedure was further developed into a two steps process in which attachment to the FMS spacer was executed in a controlled and site directed manner. In the first step, the FMS spacer was coupled to the OXM (on resin partially protected OXM), then cleaved followed by de-protection and purification of FMS-OXM (by RP-HPLC). The second step was the attachment of PEG30-SH to the purified homogeneous FMS-OXM. The final conjugated product is further purified by RP-HPLC. Additional purification steps may be applied such as Ion exchange or SEC-HPLC or any other purification step.

Three peptides on resin were synthesized using Fmoc solid phase strategy. For synthesis of the homogeneous conjugate connected by amino acid lysine in position 12 or 30 of the OXM, a selective protecting group was applied for either Lys12 or Lys30 of OXM as ivDde (1-[(4,4-dimethyl-2,6-dioxocyclohex-1-ylidine)ethyl]), which can be removed under basic conditions while the rest of the peptide is still on the resin with the other protective groups.

Therefore, three resin-bound OXMs were synthesized: N-terminal—using protection groups suitable for solid phase synthesis with Fmoc strategy (usually Boc protecting group is used for the ε amine) and Lys$_{12}$ or Lys$_{30}$ with ivDde protection group. These OXM peptides were intended for further selective coupling with the FMS linker.

Homogenous conjugates performed as 'on resin synthesis'. The conjugate synthesized in two steps: 1. Coupling between the OXM and FMS, cleavage and purification 2. Pegylation of OXM-FMS with PEG$_{30}$-SH. In this procedure, the coupling of the FMS linker is done with the OXM, while it is bound to the resin. The OXM was fully protected, allowing the specific un-protected desired amino site on OXM to react with the NHS moiety. The purified FMS-OXM was attached to the PEG-SH. The crude conjugate was purified using HPLC (RP or Cation exchange or both).

Example 2

In-Vitro Characterization of GLP-1 Receptor Activation

GLP-1 receptor binding activation of PEG-FMS-OXM (MOD-6030; heterogenous) and 3 different homogeneous variants of PEG-FMS-OXM; the amino (MOD-6031), Lys12 and Lys30 were assessed using two different cell-lines over expressing GLP-1 receptor; the Millipore HTS163C2 cell line and the cAMP Hunter™ CHO-K1 GLP1R. The potencies were determined by calculating the EC50 of each variant, followed by calculating the relative potency of each variant to the heterogeneous (MOD-6030) version (dividing EC50 of each homogenous variant by the EC50 of the heterogeneous version and multiplying it by 100). The EC50 values and calculated relative potencies are presented in table 3. For comparison, the binding affinity of OXM and GLP-1 to GLP-1 receptor of cAMP Hunter CHO-K1 GLP1R cell line were measured.

TABLE 3

GLP-1 and Glucagon receptors binding activation

|  | Millipore HTS163C2 | | cAMP Hunter ™ CHO-K1 GLP1R | | cAMP Hunter ™ CHO-K1 GCGR | |
| --- | --- | --- | --- | --- | --- | --- |
|  | EC50 (nM) | Relative potency to heterogeneous (%) | EC50 (nM) | Relative potency to heterogeneous (%) | EC50 (nM) | Relative potency to heterogeneous (%) |
| Hetero PEG$_{30}$-FMS-OXM | 76.2 | 100 | 8.14 ± 1.35 | 100 | 11.32 ± 3.26 | 100 |
| PEG$_{30}$-FMS-OXM AMINO | 55.2 | 72.24 | 8.07 ± 0.21 | 99.1 | 10.31 ± 2.87 | 91.1 |
| PEG$_{30}$-FMS-OXM Lys$_{12}$ | 179 | 234.9 | 9.42 ± 1.77 | 115.7 | 20.21 ± 4.12 | 178.5 |
| PEG$_{30}$-FMS-OXM Lys$_{30}$ | 307 | 402.9 | 17.34 ± 2.37 | 213.0 | 6.12 ± 1.75 | 54.1 |
| Oxyntomodulin (OXM) |  |  | 1.38 ± 0.68 |  | 1.02 ± 0.32 |  |
| GLP-1 |  |  | 0.016 ± 0.006 |  | NA |  |
| Glucagon |  |  | NA |  | 0.04 ± 0.011 |  |

The relative potencies of the homogeneous variants were compared to the heterogeneous version and summarized in Table 3. Comparable bioactivity of the amino variant and the heterogeneous variant exhibited a relative potency of 72.2% and 99.1% measured using the Millipore HTS163C2 and the cAMP Hunter™ CHO-K1 GLP1R, respectively.

The Lys12 and Lys30 variants had shown 2 and 4 fold reduction of GLP-1 receptor binding activation using the Millipore HTS163C2 cell line while only showing minor and a 2 fold reduction, respectively, using the cAMP Hunter™ CHO-K1 GLP1R cell line. The fact the amino variant demonstrated superior binding activity compared to the other variants is unexpected as the N-terminus of OXM was reported to be involved in the binding of OXM to the GLP-1 receptor (Druce et al., 2008). Overall, comparable bioactivity was shown for the amino variant and the heterogeneous variant. GLP-1 receptor binding activations of OXM and GLP-1 peptides were measured. It was found that OXM and GLP-1 had shown higher receptor binding activation by 5.9 and 508.7 fold compared to the heterogeneous PEG30-FMS-OXM.

Example 3

In-Vitro Characterization of Glucagon Receptor Activation

Binding affinities of PEG-FMS-OXM variants to the glucagon receptor were determined using cAMP Hunter™ CHO-K1 GCGR cell-line that over expresses glucagon-receptor. This cell line was used to characterize the heterogeneous PEG-FMS-OXM (MOD-6030) and 3 different homogeneous variants of PEG-FMS-OXM; the amino (MOD-6031), Lys12 and Lys30. The potencies were determined by calculating the EC50 of each variant, followed by calculating the relative potency of each variant to the heterogeneous version (dividing EC50 of each homogenous variant by the EC50 of the heterogeneous version and multiplying the value by 100). The EC50 values and calculated relative potencies are presented in table 3. Amino variant showed comparable binding activity to the heterogeneous version. The Lys30 variant showed the highest bioactivity and Lys12 had shown 1.8 fold reductions. Glucagon receptor binding activations of OXM and glucagon peptides were measured. It was found that OXM and glucagon had shown higher receptor binding activation by 11.1 and 283 fold compared to the heterogeneous PEG30-FMS-OXM.

Example 4

Induction of Glucose Tolerance by PEG30-FMS-OXM Variants

In order to evaluate the in vivo activity of the heterogeneous PEG$_{30}$-FMS-OXM and the three PEG$_{30}$-FMS-OXM variants (amino, Lys$_{12}$ and Lys$_{30}$), the IPGTT model was applied. Overnight fasted C57BL/6 mice were injected IP with the different compounds and a vehicle (PEG-SH) followed by IP injection of glucose and measurement of blood glucose levels from the tail vein using a glucometer. PEG-SH (238.10 nmol/kg), heterogeneous and homogeneous PEG$_{30}$-FMS-OXM, 100 nmol/kg peptide content) were administered IP 15 min prior to glucose IP injection (1.5 gr/kg). All the compounds induced glucose tolerance compared to vehicle group. Surprisingly, the homogeneous amino variant was slightly less potent compared to the two other variants and to the heterogeneous PEG$_{30}$-FMS-OXM (table 4 FIG. 3) reflected by the slightly higher glucose AUC compared to other variants, as opposed to the in-vitro activity results. Yet, all variants significantly improved glucose tolerance as compared to the vehicle PEG-SH control.

TABLE 4

Glucose tolerance in C57BL/6 mice

| | AUC (−60-180) | % AUC from control | AUC (0-180) | % AUC from control |
|---|---|---|---|---|
| PEG-SH | 26857 | 100 | 22522 | 100 |
| Heterogeneous PEG$_{30}$-FMS-OXM | 18200 | 67.8 | 13541 | 60.1 |
| PEG30-FMS-OXM AMINO variant | 19891 | 74.1 | 15781 | 70.1 |
| PEG30-FMS-OXM Lys12 variant | 17652 | 65.7 | 13953 | 62.0 |
| PEG30-FMS-OXM Lys30 variant | 17818 | 66.3 | 13159 | 58.4 |

Figure 3:
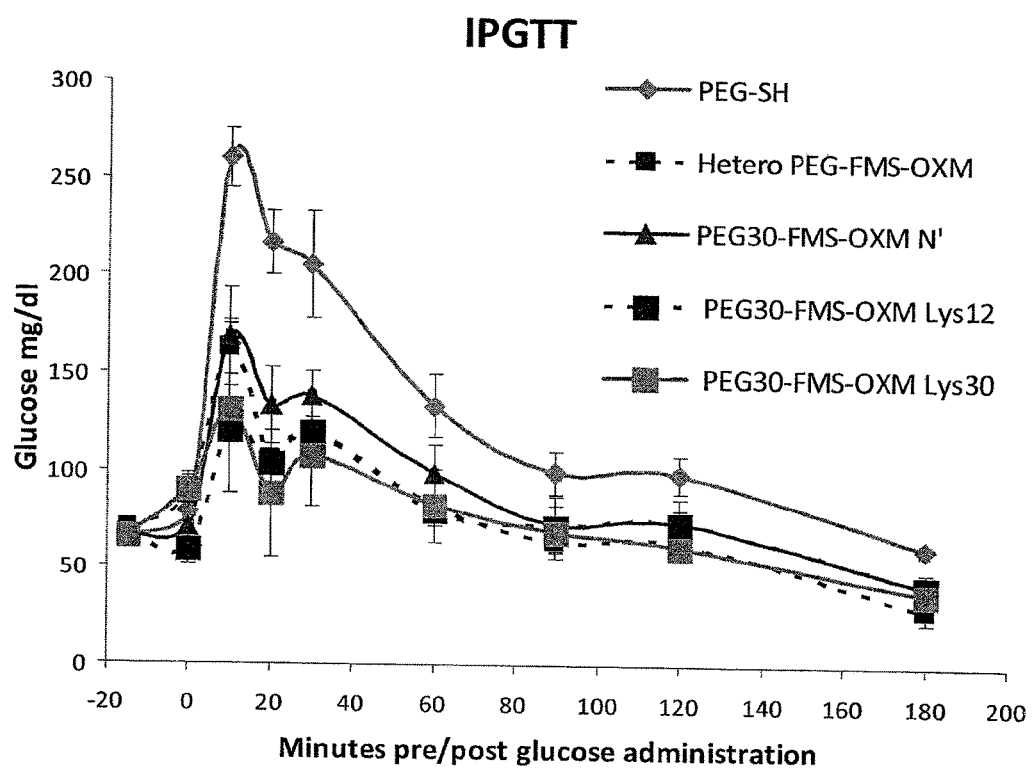
FIG. 3 is a graph showing the in vivo activity of the heterogeneous $PEG_{30}$-FMS-OXM and the three $PEG_{30}$-FMS-OXM variants (amino, Lys12 and Lys30) in the IPGTT model. All the compounds induced glucose tolerance compared to vehicle group.

The heterogeneous and homogeneous variants of the reversible PEG$_{30}$-FMS-OXM were shown to be active both in-vitro and in the IPGTT model in-vivo. Surprisingly, the in-vitro results were not aligned with what is suggested in the literature, that the N-terminus of native OXM is involved in the peptide binding to the GLP-1 receptor; therefore, it was expected that the amino terminus variant would show the lowest potency both in-vitro and in-vivo. However, the homogeneous amino variant of PEG$_{30}$-FMS-OXM demonstrated improved GLP-1 receptor activation compared to the two other homogeneous variants using two different cell lines (table 3) while demonstrating comparable efficacy in the IPGTT in vivo model. The IPGTT in vivo model seems to present comparable activity (considering the variability between the animals). Although different in-vitro binding activates to the GLP-1R and the GCGR were observed between the different PEG30-FMS-OXM variants, comparable ability to induce glucose tolerance was shown (table 3 and 4). Unexpectedly, the superior in vitro activity of homogeneous amino PEG$_{30}$-FMS-OXM as shown in the cAMP induction assay was not reflected in the in vivo IP glucose tolerance test. The homogeneous amino variants PEG$_{30}$-FMS-OXM showed the lowest glucose tolerance profile compared to the two other variants and to the heterogeneous PEG$_{30}$-FMS-OXM. However, it still showed significant glucose tolerance effect in comparison to the vehicle (FIG. 3).

Example 5

Improvement of Body Weight, Glycemic and Lipid Profiles by PEG30-FMS-OXM Variants in Ob/Ob Mice Model The ob/ob mice model exhibits a mutation of the ob gene such that they cannot produce leptin and develop a phenotype characterized by hyperinsulinaemia, obesity, hyperphagia, insulin resistance and subsequently hyperglycaemia. These mice were used as a genetic model of diabetes in two different studies in order to evaluate the efficacy of PEG30-FMS-OXM (Heterogeneous) and the three homogeneous variants of PEG30-FMS-OXM (amino, Lys12 and Lys30).

Figure 4:
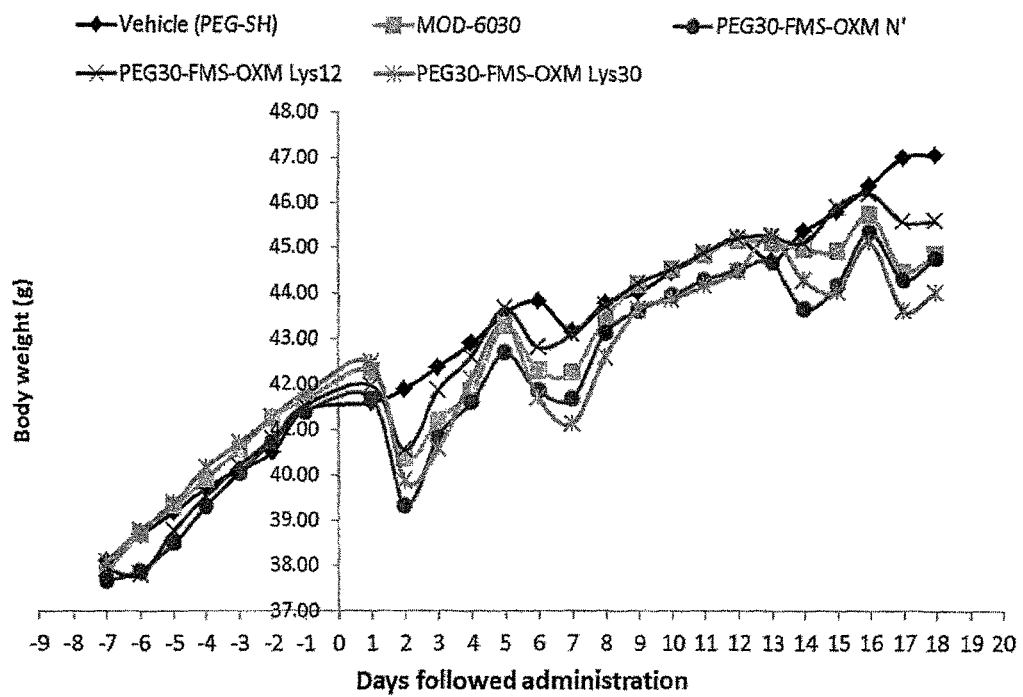
FIG. 4 shows the effect of the heterogeneous PEG30-FMS-OXM and the three PEG30-FMS-OXM variants (amino, Lys12 and Lys30) on body weight in male ob/ob mice.
Figure 5:
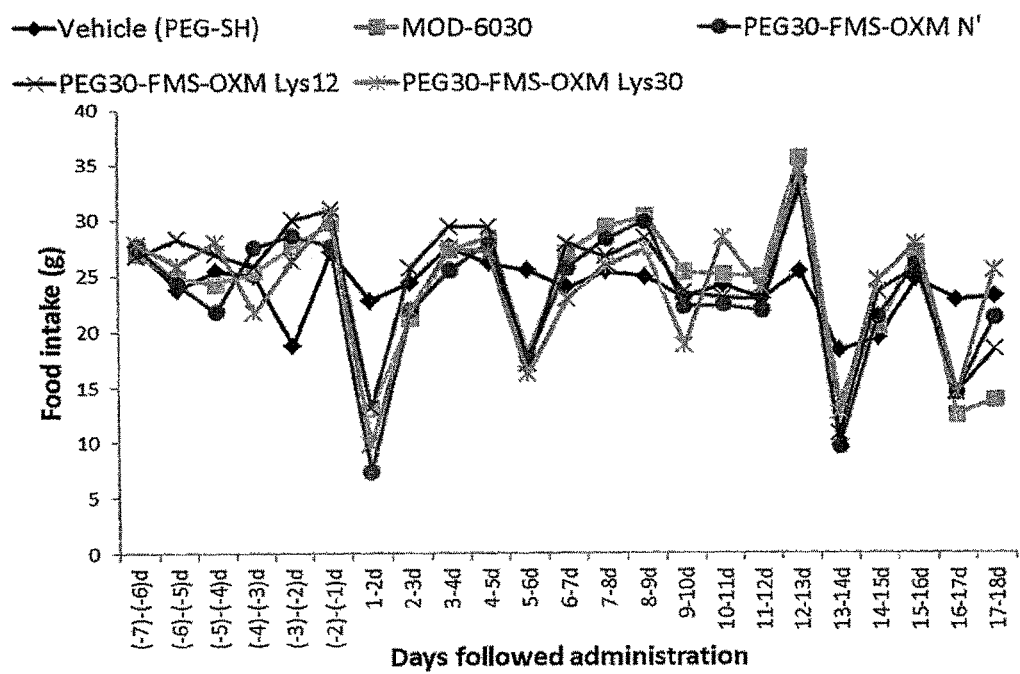
FIG. 5 shows the effect of the heterogeneous PEG30-FMS-OXM and the three PEG30-FMS-OXM variants (amino, Lys12 and Lys30) on food intake in male ob/ob mice.
Figure 6:
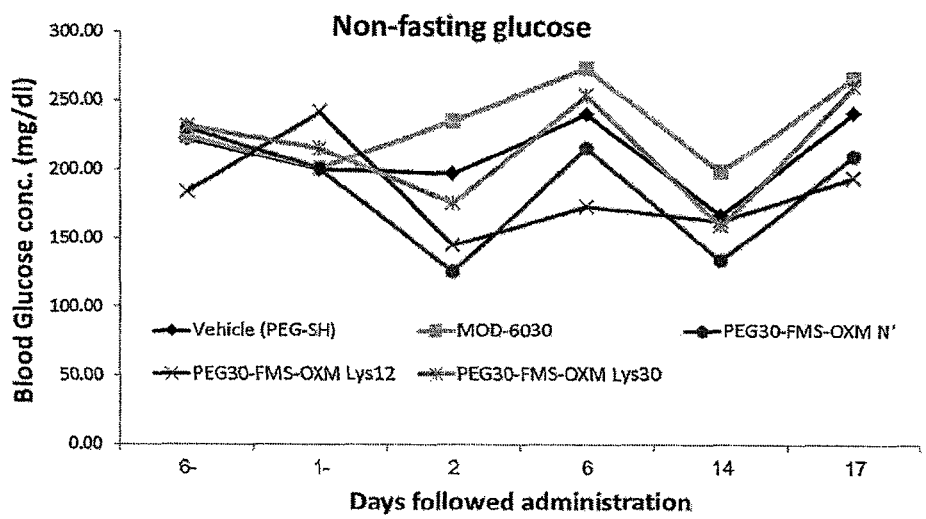
FIG. 6 shows the effect of the heterogeneous PEG30-FMS-OXM and the three PEG30-FMS-OXM variants (amino, Lys12 and Lys30) on non-fasting and fasting glucose in male ob/ob mice.
Figure 6:
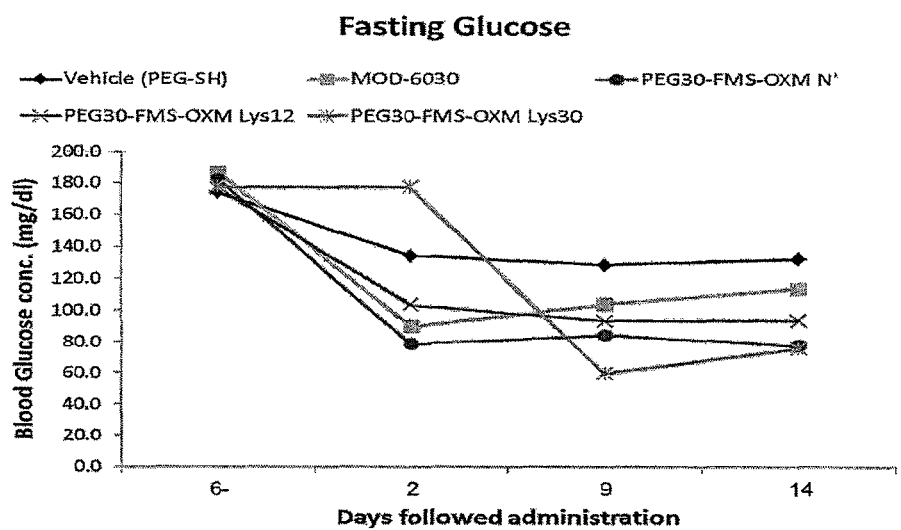

Study 1: This study compared the efficacy of homogeneous variants (amino, Lys12 and Lys30) and the heterogeneous MOD-6030 when administered at 2000 nmol/kg. Reductions of body weight were obtained for all tested articles compared to vehicle (PEG-SH) group with final reduction (on day 18) of 3.1%, 4.7%, 4.9% and 6.5% for Lys12, MOD-6030, amino and Lys30 variants, respectively (FIG. 4). Body weight reductions were observed following drug injection on days 1, 5, 13 and 16 (FIG. 4). Reduction of food intake was observed for all treated groups following drug administration (except day 9) (FIG. 5). Measurement of glycemic parameters along the study had shown improvement of non-fasting glucose (FIG. 6a) for amino and Lys12 treated groups and improvement of fasting glucose for all treated groups (FIG. 6b). All treated groups showed significantly lower level of insulin compared to the control. Of note, the administered dose in this study was 2000 nmol/kg which is the lower effective dose of MOD-6030 and thus the improvement of body weight, food intake and glycemic profile were relatively moderate. Unexpectedly the amino variant was the only variant which showed superior efficacies in the ability to reduce weight, inhibit food intake and to improve glycemic control. From a manufacturing perspective, on resin synthesis of the amino variant is the most straight forward procedure considering that the peptide in solid phase synthesis is extended from the amino terminus. The terminal amine has preferred availability for coupling than the internal amine groups of the Lysine at positions 12 and 30. This accessibility is reflected in the higher manufacturing yields of the amino variant as compared to the Lys12 and Lys30 variants. An additional benefit is that the synthesis towards the amino variant remains unchanged relative to OXM synthesis for the heterogeneous variant, while the synthesis of Lys12 and Lys30 variants was modified by changing the Lys used for the peptide synthesis and by the addition of a selective cleavage step (selectively removing the protecting group of the Lys). The OXM synthesis as previously developed for the heterogeneous was already optimized to achieve better yield and robustness. Overall, from a manufacturing perspective, synthesis of amino variant on-resin is straight forward and possesses an advantage over the alternative variants. Being a homogenous variant, it also has an advantage over a heterogeneous variant in that it is more suitable for drug development and drug treatment.

Figure 7:
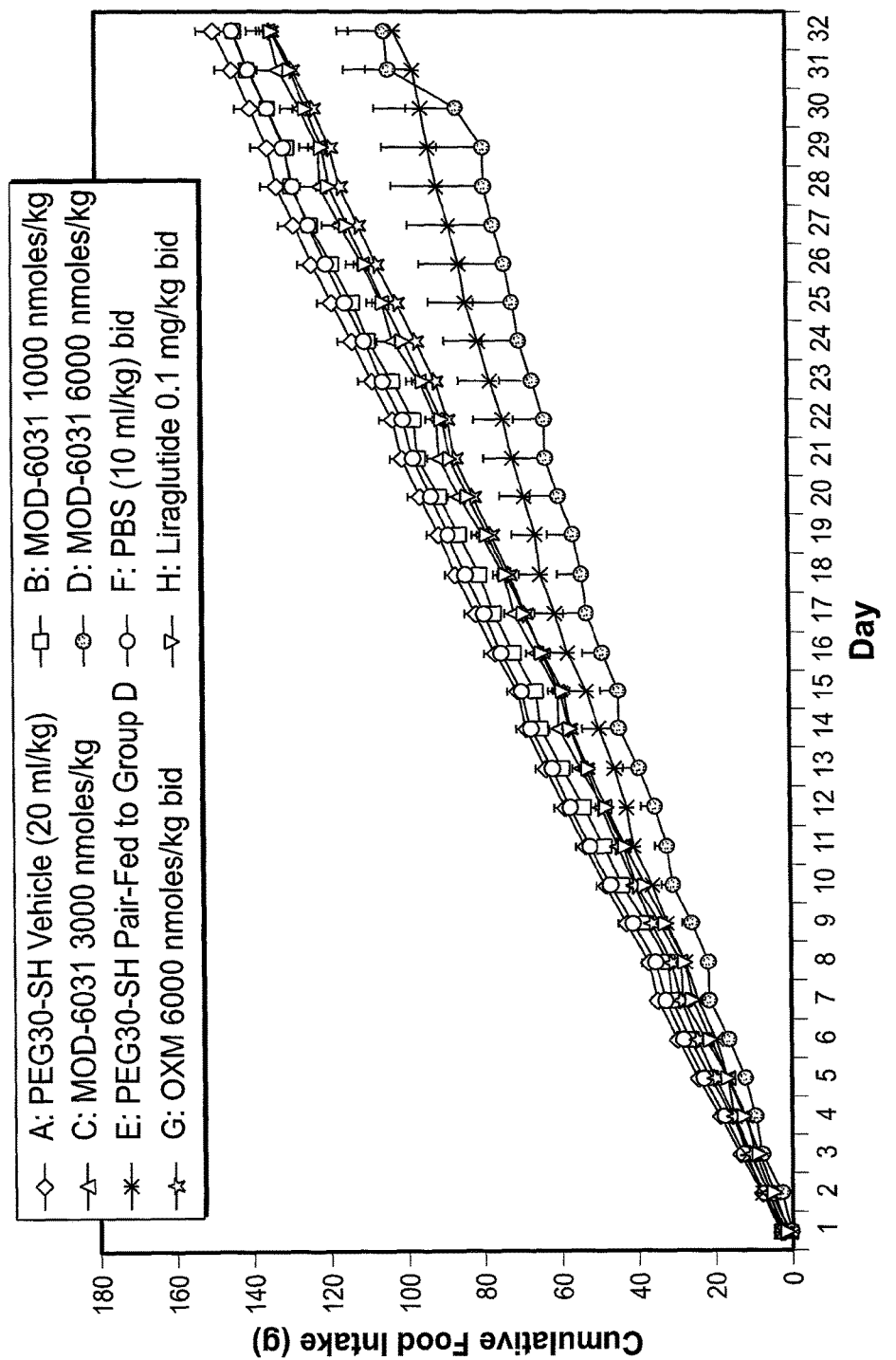
FIG. 7 shows the effect of MOD-6031, OXM and liraglutide on cumulative food intake in male ob/ob mice.
Figure 8:
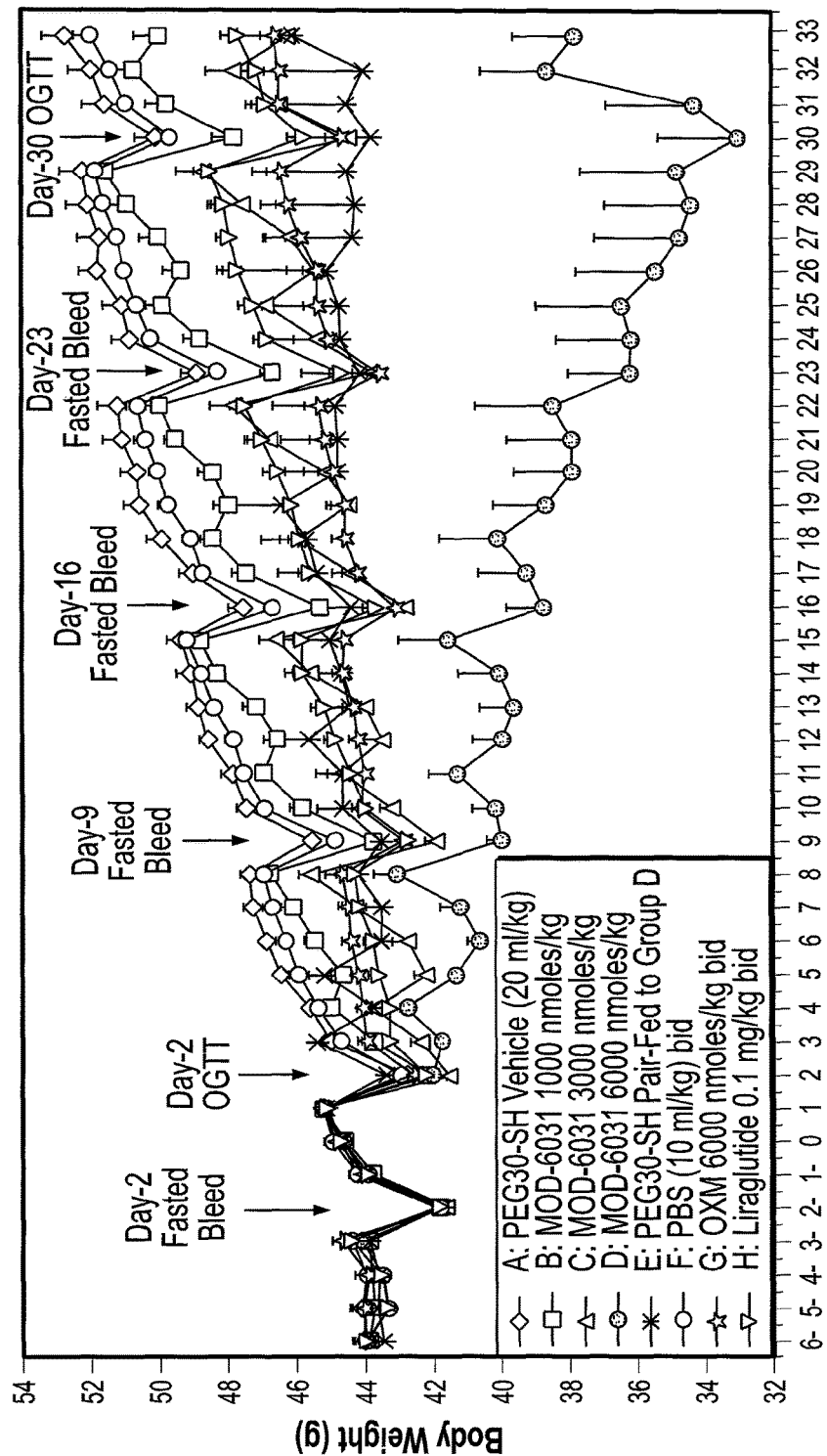
FIG. 8 shows the effect of MOD-6031, OXM and liraglutide on body weight in male ob/ob mice.
Figure 9:
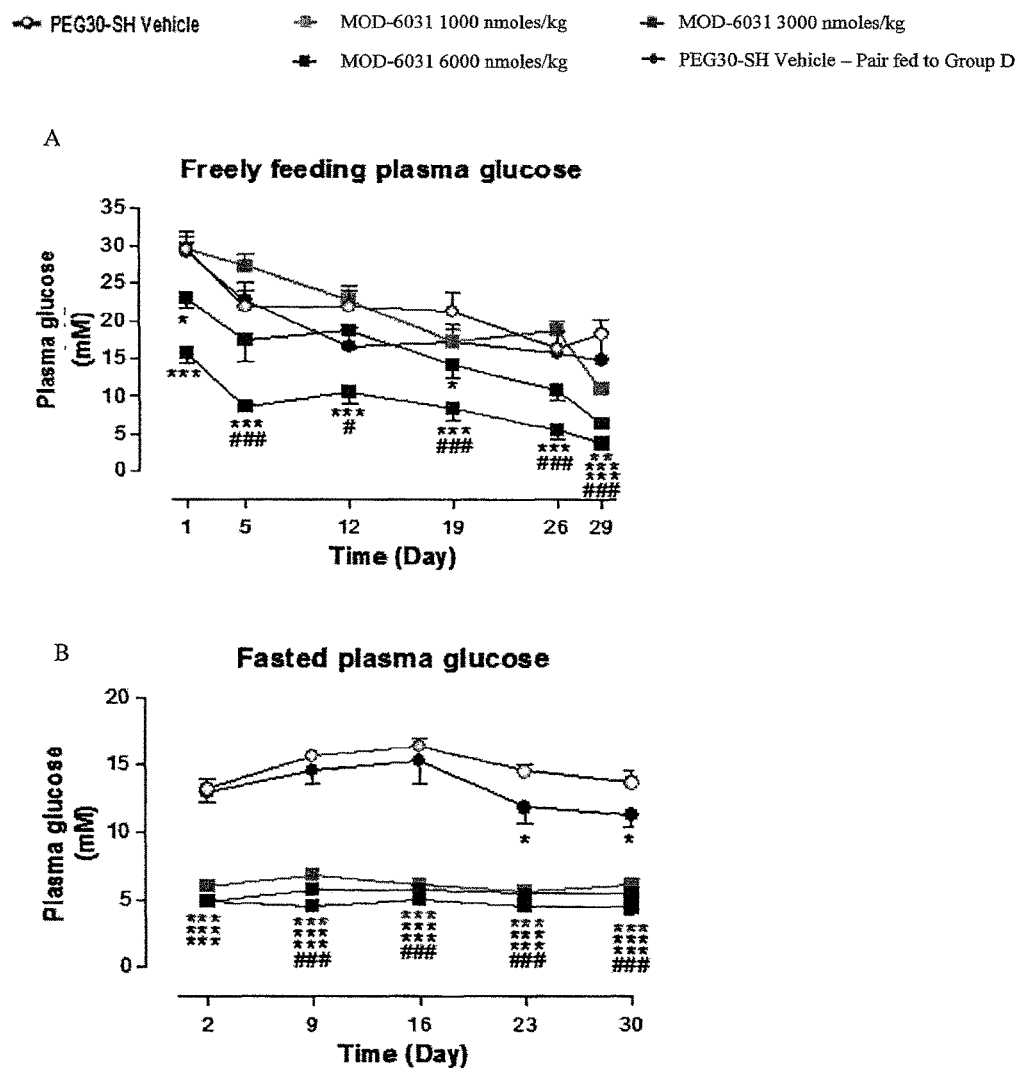
FIG. 9 shows the effect of MOD-6031, OXM and liraglutide on freely feeding and fasted plasma glucose in male ob/ob mice.
Figure 10:
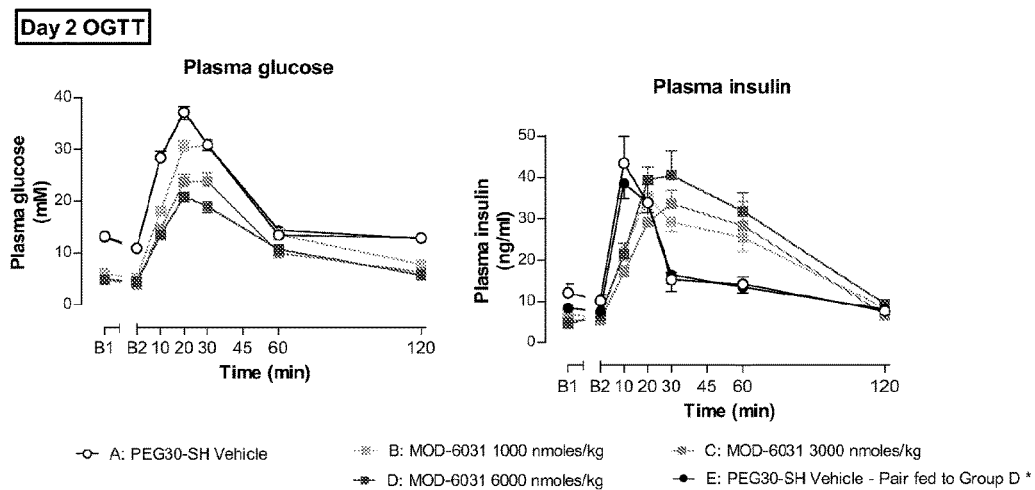
FIG. 10 shows the effect of MOD-6031 and pair fed group on glucose tolerance (2 g/kg po) on day 2 of the study, in male ob/ob mice.
Figure 11:
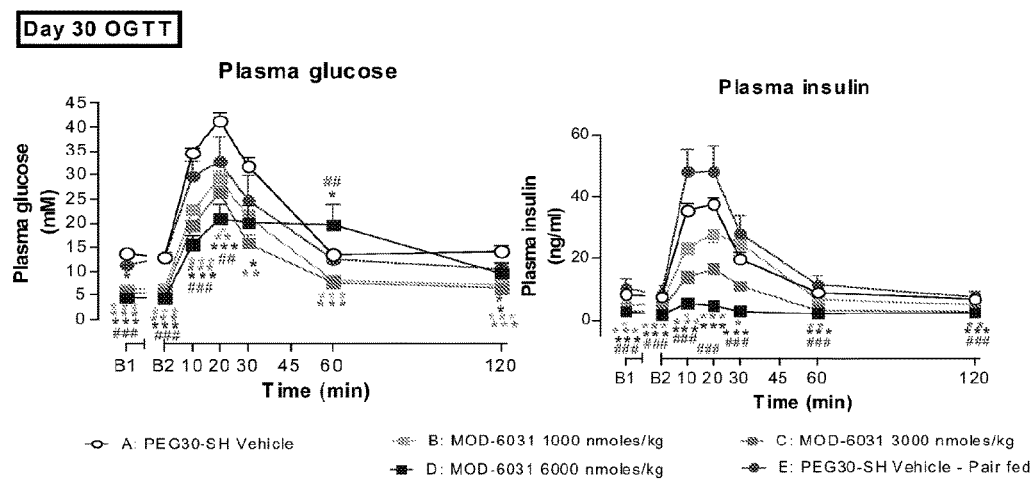
FIG. 11 shows the effect of MOD-6031 and pair fed group on glucose tolerance (2 g/kg po) on day 30 of the study, in male ob/ob mice
Figure 12:
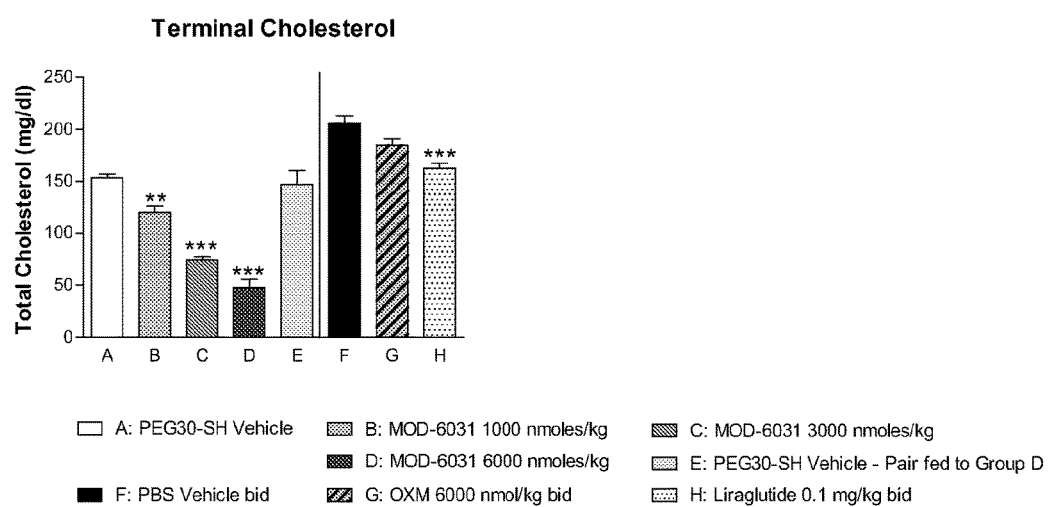
FIG. 12 shows the effect of MOD-6031, OXM and liraglutide on terminal plasma cholesterol in male ob/ob mice

Study 2: This study investigated the chronic effect of twice a week administration of MOD-6031 (the amino variants) at 1000, 3000 and 6000 nmol/kg, on pharmacological and pharmacokinetic parameters in ob/ob mice model, while OXM and liraglutide (long-acting GLP-1 receptor agonist) were evaluated as reference compounds. The measured pharmacological parameters were body weight, food and water intake, glucose control and lipid profile. Twice a week administration of high dose of MOD-6031 (6000 nmol/kg) significantly reduced food intake and body weight (FIGS. 7, 8), while the lower doses (3000 and 1000 nmol/kg) had shown lower effects. At the conclusion of the study (day 33) animals of 1000, 3000 and 6000 nmol/kg had shown body weight reduction of 5.2%, 12.3% and 28.3%, respectively. The pair fed group, which were paired to the high dose group and ate equal amount of food (except the fasting days), had a body weight reduction of 12.7% while undergoing similar food intake. This phenomenon can be attributed to the ability of the amino variant of PEG30-FMS-OXM to increase energy expenditure and thus animals that were treated with 6000 nmol/kg of the amino variant had an increased reduction of body weight over the body weight reduction of its pair fed group. Over the study OXM and liraglutide both significantly reduced body weight, by 10.3% and 8.3% respectively. Measurement of glycemic profile which monitored non-fasting glucose on days 1, 5, 12, 19, 26 and 29 and fasting glucose on days 2, 9, 16, 23 and 30 had shown significant improvement of these parameters, especially for the 6000 nmol/kg (FIG. 9a, 9b). Oral glucose tolerant test (OGTT) studies were performed on days 2 and day 30 (FIGS. 10 and 11, respectively). The results showed that MOD-6031 (the amino variant) significantly and dose-dependently improved glucose tolerance with plasma glucose being significantly reduced in the 1000, 3000 and 6000 nmoles/kg groups. Animals pair-fed to the highest MOD-6031 dose exhibited a glucose excursion post glucose dose that was not significantly different to controls at any of the time points tested. On Day 2 of the OGTT studies, the improved glucose profile was associated with a delay of the insulin response, which slightly delayed and gave higher stimulation for AUC 0-120 min (FIG. 10). This can be due to inhibition of gastric emptying induced by MOD-6031's pharmacological activity which results in a delay in glucose release into the blood and a second insulin secretion phase. Day 30 of the OGTT studies was associated with a reduced insulin response compared to controls showing that the compound improved insulin sensitivity (FIG. 11). In addition, MOD-6031 dose-dependently reduced terminal cholesterol; the reduction observed with the 6000 nmoles/kg dose of MOD-6031 was significantly greater than that of pair-fed counterparts (FIG. 12). All of these pharmacological improvements in body weight, food intake, glycemic and lipid profiles were greater not only than animals treated bi-daily with OXM or liraglutide, but they were also significantly greater than the effects observed in pair-fed counterparts.

Terminal blood level of MOD-6031(PEG-FMS-OXM) and its hydrolyzed compounds (PEG-FMS and OXM) were measured using an LC-MS/MS qualified method. Results showed dose dependent concentrations for the MOD-6031 treated groups (Table 5). Comparison of this data to compound levels on day 2 (following single administration) showed that OXM peptide were not accumulated during the study period when administered twice a week. PEG-FMS and PEG-FMS-OXM showed moderate accumulation over the study (Table 5). The actual concentration of MOD-6031 and OXM peptide for the top dose of MOD-6031 at 24 h post last injection (Day 33) were 490 μg/ml and 0.37 μg/ml, respectively. All samples from control animals were below the lower limit of the assay.

TABLE 5

Comparison of Plasma Concentrations 24 Hours Following Single Dose (Day 2) and Last Injection of Repeat MOD-6031 Dosing Regimen (Day 33).

| | compound: | Day 2 | Day 33 | Increased by |
|---|---|---|---|---|
| Dose: | | | | |
| 1000 | PEG-FMS-OXM | 51.57 | 67.51 | 1.31 |
| 3000 | PEG-FMS-OXM | 183.33 | 266.75 | 1.46 |
| 6000 | PEG-FMS-OXM | 296.33 | 493.60 | 1.67 |
| 1000 | OXM | 0.07 | 0.09 | 1.29 |
| 3000 | OXM | 0.23 | 0.23 | 1.00 |
| 6000 | OXM | 0.38 | 0.37 | 0.97 |
| Dose*: | | | | |
| 1000 | PEG-FMS | 65.73 | 78.04 | 1.19 |
| 3000 | PEG-FMS | 211.67 | 295.75 | 1.40 |
| 6000 | PEG-FMS | 359.33 | 740.00 | 2.06 |

*Doses including impurities are 1515, 4545, and 9090 nmol/kg

Example 6

Improvement of Pharmacokinetic Parameters by MOD-6031 Variant in Ob/Ob Mice Model Three groups (n=12) of ob/ob mice were singly administered with 1000, 3000 and 6000 nmol/kg of MOD-6031 and were bled at 4, 8, 24, 36, 48, 72, 96 and 120 h post administration (n=3 per time point) for PK analysis and the quantity of MOD-6031 and its compounds concentrations determined LC-MS/MS method. Pharmacokinetic parameters such as Cmax, Tmax, AUC, T1/2Cl and Vz were calculated for MOD-6031 (PEG-FMS-OXM) and its hydrolyzed products; PEG-FMS and OXM, these parameters are presented in Table 6a, 6b and 6c, respectively. AUC 0-∞ was within 15% of AUC 0-t for all components at all doses, indicating that the sampling schedule was adequate to characterize the pharmacokinetic profile of each component. For all three components, exposure appeared to be dose-proportional. In general, Cmax and AUC 0-t increased with dose and in approximately the same proportion as the increase in dose.

Parameters for each component are expressed in molar concentrations in Table 7. Cmax values were approximately equivalent for PEG-FMS-OXM and PEG-FMS and lower for OXM. The observed $T_{1/2}$ for PEG-FMS-OXM and OXM were approximately 9 and 12 hours, respectively. The terminal $T_{1/2}$ for PEG-FMS was much longer, approximately 30 hours. All samples from control animals and all samples collected prior to dosing were below the lower limit of the assay.

The pharmacokinetic and pharmacological data confirm the long acting properties of MOD-6031. Twice a week dose of 3000 nmoles/kg of MOD-6031 significantly reduced body weight and food consumption which was comparable to twice a day of the OXM peptide treatment arm administered at a 6000 nmoles/kg dose leading also to a significant reduction in drug load.

TABLE 6a

PEG-FMS-OXM Pharmacokinetic Parameters Following SC Injection of 1000, 3000, or 6000 nmoles/kg

| Parameter | Units | 1000 nmol/kg, 34.9 mg/kg | 3000 nmol/kg, 105 mg/kg | 6000 nmol/kg, 210 mg/kg |
|---|---|---|---|---|
| Cmax | µg/mL | 70.2 | 224 | 311 |
| Tmax | hr | 8.00 | 8.00 | 8.00 |
| $AUC_{0-t}$ | hr * µg/mL | 1840 | 6330 | 10700 |
| $AUC_{0-\infty}$ | hr * µg/mL | 1850 | 6330 | 10700 |
| $T_{1/2}$ | hr | 8.57 | 8.80 | 12.3 |
| CL/F | mL/hr/kg | 18.9 | 16.5 | 19.5 |
| Vz/F | mL/kg | 234 | 210 | 346 |
| Cmax/D | (µg/mL)/(mg/kg) | 2.01 | 2.14 | 1.48 |
| $AUC_{1-\infty}$/D | (hr * µg/mL)/(mg/kg) | 52.9 | 60.5 | 51.3 |

TABLE 6b

PEG-FMS Pharmacokinetic Parameters Following SC Injection of 1000, 3000, or 6000 nmoles/kg of MOD-6031

| Parameter | Units | 1000 nmol/kg, 34.9 mg/kg | 3000 nmol/kg, 105 mg/kg | 6000 nmol/kg, 210 mg/kg |
|---|---|---|---|---|
| Cmax | pg/mL | 65.7 | 212 | 407 |
| Tmax | hr | 24.0 | 24.0 | 36.0 |
| $AUC_{0-t}$ | hr * µg/mL | 3060 | 10700 | 22800 |
| $AUC_{0-\infty}$ | hr * µg/mL | 3280 | 11200 | 25800 |
| $T_{1/2}$ | hr | 33.5 | 22.8 | 35.0 |
| CL/F | mL/hr/kg | 14.0 | 12.4 | 10.8 |
| Vz/F | mL/kg | 678 | 408 | 544 |
| Cmax/D | (µg/mL)/(mg/kg) | 1.43 | 1.52 | 1.46 |
| $AUC_{1-\infty}$/D | (hr * µg/mL)/(mg/kg) | 71.3 | 80.5 | 92.8 |

Note: Due to PEG-FMS impurity in the dosing solutions, the administered doses of PEG-FMS (MOD-6031 plus PEG-FMS impurity) were 1515, 4545, and 9090 nmol/kg instead of 1000, 3000 and 6000 nmol/kg, respectively.

TABLE 6c

OXM Pharmacokinetics Parameters Following SC Injection of 1000, 3000, or 6000 nmoles/kg of MOD-6031

| Parameter | Units | 1000 nmol/kg, 34.9 mg/kg | 3000 nmol/kg, 105 mg/kg | 6000 nmol/kg, 210 mg/kg |
|---|---|---|---|---|
| Cmax | µg/ml | 0.159 | 0.365 | 0.749 |
| Tmax | hr | 8.00 | 8.00 | 8.00 |
| $AUC_{0-t}$ | hr * µg/mL | 3.19 | 9.29 | 18.5 |
| $AUC_{0-\infty}$ | hr * µg/mL | NC | 9.42 | 18.5 |
| $T_{1/2}$ | hr | NC | 11.7 | 11.8 |
| CL/F | mL/hr/kg | NC | 1420 | 1440 |
| Vz/F | mL/kg | NC | 23900 | 24400 |
| Cmax/D | (µg/mL)/(mg/kg) | 0.0357 | 0.0274 | 0.0280 |
| $AUC_{1-\infty}$/D | (hr * µg/mL)/(mg/kg) | NC | 0.705 | 0.694 |

NC = due to the shape of the concentration versus time profile, parameters could not be calculated

TABLE 7

Pharmacokinetic Parameters Comparing the Three Components on a Molar Basis

| Dose[a] nmol/kg | Component | $C_{max}$ nmol/mL | $C_{max}/D$ (nmol/mL)/ (μmol/kg) | $AUC_{0-t}$ hr*nmol/mL | $AUC_{0-t}/D$ (hr*nmol/mL)/ (μmol/kg) | $T_{1/2}$ Hr |
|---|---|---|---|---|---|---|
| 1000 | PEG-FMS-OXM | 2.01 | 2.01 | 52.6 | 52.6 | 8.57 |
| 1515 | PEG-FMS[a] | 2.16 | 1.43 | 100 | 66.0 | 33.5 |
| 1000 | OXM | 0.0357 | 0.0357 | 0.716 | 0.716 | NC |
| 3000 | PEG-FMS-OXM | 6.42 | 2.14 | 181 | 60.3 | 8.80 |
| 4545 | PEG-FMS[a] | 6.96 | 1.53 | 353 | 77.7 | 22.8 |
| 3000 | OXM | 0.0821 | 0.0273 | 2.09 | 0.697 | 11.7 |
| 6000 | PEG-FMS-OXM | 8.90 | 1.48 | 307 | 51.2 | 12.3 |
| 9090 | PEG-FMS[a] | 13.4 | 1.47 | 750 | 82.5 | 35.0 |
| 6000 | OXM | 0.168 | 0.0280 | 4.15 | 0.692 | 11.8 |

[a]Doses of PEG-FMS accounts for impurities (MOD-6031 plus PEG-FMS impurity).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A conjugate consisting of an oxyntomodulin, a polyethylene glycol polymer (PEG polymer) and 9-fluorenylmethoxycarbonyl (Fmoc) or 2-sulfo-9-fluorenylmethoxycarbonyl (FMS), wherein said PEG polymer is attached to the amino terminus of said oxyntomodulin or to a lysine residue on position number twelve ($Lys_{12}$) of said oxyntomodulin, via Fmoc or FMS.

2. The conjugate of claim 1, wherein said oxyntomodulin consists of the amino acid sequence set forth in SEQ ID NO: 1.

3. The conjugate of claim 1, wherein said PEG polymer is a PEG polymer with a sulfhydryl moiety.

4. The conjugate of claim 1, wherein said PEG polymer is PEG30.

5. A pharmaceutical composition comprising the conjugate of claim 1 and a pharmaceutical acceptable carrier.

6. A method of inducing glucose tolerance in a subject in need thereof, or increasing insulin sensitivity in a subject in need thereof, or inducing glycemic control in a subject in need thereof, or reducing insulin resistance in a subject in need thereof, the method comprising administering the pharmaceutical composition of claim 5.

7. A method of reducing food intake in a subject in need thereof, or reducing body weight in a subject in need thereof, or for increasing energy expenditure in a subject in need thereof, or improving the cholesterol levels in a subject in need thereof, the method comprising administering the pharmaceutical composition of claim 5.

* * * * *

SEQUENCE LISTING

<160> NUMBER OF SEQ ID NOS: 1

<210> SEQ ID NO 1
<211> LENGTH: 37
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35